United States Patent [19]

Duggan

[11] Patent Number: 4,873,345

[45] Date of Patent: Oct. 10, 1989

[54] PROCESS FOR THE PREPARATION OF 5'-OXA, 5'-THIA, 5'-AZA HMG-COA REDUCTASE INHIBITORS

[75] Inventor: Mark E. Duggan, Wynnewood, Pa.

[73] Assignee: Merck & Co., Inc., Rahway, N.J.

[21] Appl. No.: 250,525

[22] Filed: Sep. 29, 1988

[51] Int. Cl.[4] .................. C07D 309/10; C07D 315/00
[52] U.S. Cl. .................................... 549/214; 549/292; 549/419; 549/420
[58] Field of Search ................ 549/214, 292, 260, 63; 514/419, 420

Primary Examiner—Glennon H. Hollrah
Assistant Examiner—Mark W. Russell
Attorney, Agent, or Firm—Melvin Winokur; Joseph F. DiPrima

[57] ABSTRACT

This invention relates to novel intermediates, and novel processes for their preparation, where said intermediates are useful in a novel preparation of 5'-Oxa, 5'-Thia and 5'-Aza derivatives (I) of lovastatin and analogs thereof at the 8'-acyl side chain and 6'-position of the polyhydronaphthyl ring. Said derivatives (I) are useful in treating hypercholesterolermia.

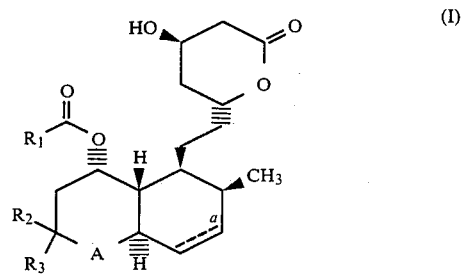

A is O, $S(O)_n$ or $N-R_{13}$.

14 Claims, No Drawings

PROCESS FOR THE PREPARATION OF 5'-OXA, 5'-THIA, 5'-AZA HMG-COA REDUCTASE INHIBITORS

BACKGROUND OF THE INVENTION

Hypercholesterolemia is known to be one of the prime risk factors for ischemic cardiovascular disease, such as arteriosclerosis. Bile acid sequestrants have been used to treat this condition; they seem to be moderately effective but they must be consumed in large quantities, i.e. several grams at a time and they are not very palatable.

MEVACOR® (lovastatin), now commercially available, is one of a group of very active antihypercholesterolemic agents that functions by limiting cholesterol biosynthesis by inhibiting the enzyme HMG-CoA reductase. In addition to the natural fermentation products, mevastatin and lovastatin, there are a variety of semi-synthetic and totally synthetic analogs thereof.

The naturally occurring compounds and their semi-synthetic analogs have the following general structural formulae:

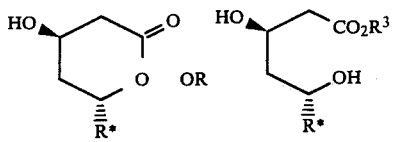

wherein:
$R^3$ is hydrogen, $C_{1-5}$ alkyl or $C_{1-5}$ alkyl substituted with a member of the group consisting of phenyl, dimethylamino, or acetylamino; and
$R^*$ is

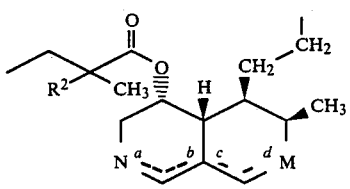

wherein N is

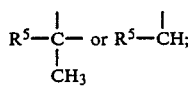

$R^5$ is H or OH; M is

$R^6$ is hydrogen or hydroxy;
$R^2$ is hydrogen or methyl; and a, b, c, and d represent single bonds, one of a, b, c or d represents a double bond, or both a and c or both b and d represent double bonds provided that when a is a double bond, N is

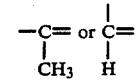

and when d is a double bond, M is

Copending patent application Ser. No. 212,767 filed June 29, 1988 discloses 6-substituted compounds of the above general formula wherein $R^*$ is

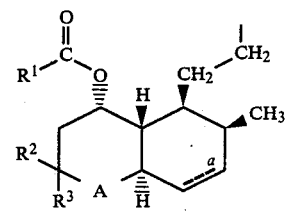

wherein A is O, $S(O)_n$ or N—$R^{13}$.

DETAILED DESCRIPTION OF THE INVENTION

This invention relates to novel intermediates of formula B:

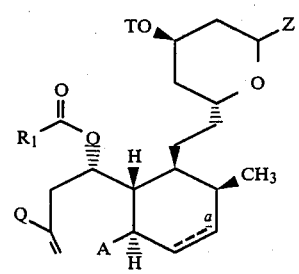

wherein:
A is HO, SH or HN—$R_N$;
Q is $CH_3$, $CH_2OT$, or H;
T is H, tert-butyldimethylsilyl, tert-butyldiphenylsilyl, trimethylsilyl, triethylsilyl, triisopropylsilyl or tetrahydropyranyl;
Z is $OCH_3$, or Z together with the carbon to which it is attached represents C=O;
$R_1$ is selected from:
  (1) $C_{1-10}$ alkyl;
  (2) substituted $C_{1-10}$ alkyl in which one or more substituent(s) is selected from
    (a) halogen,
    (b) hydroxy,
    (c) $C_{1-10}$ alkoxy,
    (d) $C_{1-5}$ alkoxycarbonyl,
    (e) $C_{1-5}$ acyloxy,
    (f) $C_{3-8}$ cycloalkyl,
    (g) phenyl,
    (h) substituted phenyl in which the substituents are X and Y,
    (i) $C_{1-10}$ alkylS(O)$_n$ in which n is 0 to 2, (j) $C_{3-8}$ cycloalkylS(O)$_n$,
(k) phenylS(O)$_n$,
(l) substituted phenylS(O)$_n$ in which the substituents are X and Y, and
(m) oxo;
(3) $C_{1-10}$ alkoxy;
(4) $C_{2-10}$ alkenyl;
(5) $C_{3-8}$ cycloalkyl;
(6) substituted $C_{3-8}$ cycloalkyl in which one substituent is selected from
  (a) $C_{1-10}$ alkyl,
  (b) substituted $C_{1-10}$ alkyl in which the substituent is selected from
    (i) halogen,
    (ii) hydroxy,
    (iii) $C_{1-10}$ alkoxy,
    (iv) $C_{1-5}$ alkoxycarbonyl,
    (v) $C_{1-5}$ acyloxy,
    (vi) phenyl,
    (vii) substituted phenyl in which the substituents are X and Y
    (viii) $C_{1-10}$ alkylS(O)$_n$,
    (ix) $C_{3-8}$ cycloalkylS(O)$_n$,
    (x) phenylS(O)$_n$,
    (xi) substituted phenylS(O)$_n$ in which the substituents are X and Y, and
    (xii) oxo,
  (c) $C_{1-10}$ alkylS(O)$_n$,
  (d) $C_{3-8}$ cycloalkylS(O)$_n$,
  (e) phenylS(O)$_n$,
  (f) substituted phenylS(O)$_n$ in which the substituents are X and Y,
  (g) halogen,
  (h) hydroxy,
  (i) $C_{1-10}$ alkoxy,
  (j) $C_{1-5}$ alkoxycarbonyl,
  (k) $C_{1-5}$ acyloxy,
  (l) phenyl, and
  (m) substituted phenyl in which the substituents are X and Y;
(7) phenyl;
(8) substituted phenyl in which the substituents are X and Y;
(9) amino;
(10) $C_{1-5}$ alkylamino;
(11) di($C_{1-5}$ alkyl)amino;
(12) phenylamino;
(13) substituted phenylamino in which the substituents are X and Y;
(14) phenyl $C_{1-10}$ alkylamino;
(15) substituted phenyl $C_{1-10}$ alkylamino in which the substituents are X and Y;
(16) a member selected from
  (a) piperidinyl,
  (b) pyrrolidinyl,
  (c) piperazinyl,
  (d) morpholinyl, and
  (e) thiomorpholinyl; and
(17) $R_5S$ in which $R_5$ is selected from
  (a) $C_{1-10}$ alkyl,
  (b) phenyl, and
  (c) substituted phenyl in which the substituents are X and Y;
$R_N$ is selected from:
  (a) $C_{1-5}$ alkyl;
  (b) phenyl$C_{1-5}$alkyl;

X and Y independently are hydrogen, halogen, trifluoromethyl, $C_{1-3}$ alkyl, nitro, cyano or a group selected from:
(1) $R_6O(CH_2)_m$ in which m is 0 to 3 and $R_6$ is hydrogen, $C_{1-3}$alkyl or hydroxy-$C_{2-3}$alkyl;
(2)

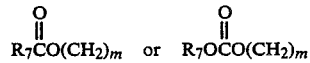

in which $R_7$ is hydrogen, $C_{1-3}$alkyl, hydroxy-$C_{2-3}$alkyl, phenyl, naphthyl, amino-$C_{1-3}$alkyl, $C_{1-3}$alkylamino-$C_{1-3}$alkyl, di($C_{1-3}$alkyl)amino-$C_{1-3}$alkyl, hydroxy-$C_{2-3}$ alkylamino-$C_{1-3}$alkyl or di(hydroxy-$C_{2-3}$alkyl) amino-$C_{1-3}$alkyl; provided that in

$R_7$ is not H;
(3)

in which $R_8$ is hydrogen, $C_{1-3}$alkyl, hydroxy-$C_{2-3}$ alkyl, $C_{1-3}$alkoxy-$C_{1-3}$alkyl, phenyl or naphthyl; (4)

 

in which $R_9$ and $R_{10}$ independently are hydrogen, $C_{1-3}$ alkyl, hydroxy-$C_{2-3}$alkyl or $R_9$ and $R_{10}$ together with the nitrogen atom to which they are attached form a heterocyclic group selected from piperidinyl, pyrrolidinyl, piperazinyl, morpholinyl or thiomorpholinyl;
(5) $R_{11}S(O)_n(CH_2)_m$ in which $R_{11}$ is hydrogen, $C_{1-3}$alkyl, amino, $C_{1-3}$alkylamino or di($C_{1-3}$alkyl)amino;
a is a single bond or a double bond; halogen is F or Cl; n is 0 to 2; and novel processes for their preparation, where said intermediates are useful in a novel preparation of 5'-oxa, 5'-thia and 5'-aza derivatives (I) of lovastatin and analogs thereof at the 8'-acyl side chain and 6'-position of the polyhydronaphthyl ring. Said derivatives (I) and analogs thereof are useful in treating hypercholesterolemia and are disclosed in copending patent application Ser. No. 212,767 filed June 29, 1988.

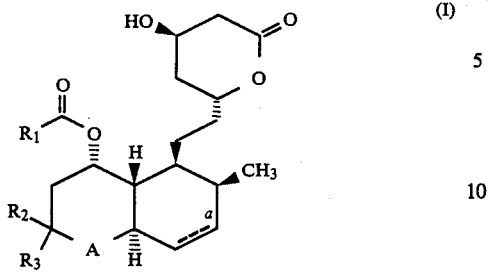

(I)

The 5'-oxa derivatives of formula (I) are prepared as shown in schemes 1, 2, 2a and 3. Scheme 1 provides the basic methodology for the incorporation of the oxa moiety in the polyhydronaphthyl ring. Schemes 2 and 2a provide for the elaboration of the substituents at the 6'-position. Scheme 3 is a modification of scheme 1 wherein a is a double bond.

The 5'-thia derivatives of formula (I) are prepared as shown in schemes 4 and 4a. Scheme 4 provides the general methodology for the incorporation of the sulfur heteroatom in the polyhydronaphthyl ring and the elaboration of the 6'-substituents. Scheme 4a describes a variation of scheme 4 wherein at least one of the $R_2$, $R_3$ substituents is methyl.

The 5'-aza derivatives of formula (I) are prepared as shown in scheme 5. A double bond may be inserted into the 3,4-position of compound (5–7) in an analogous manner to step (ix) of scheme 4.

SCHEME 1

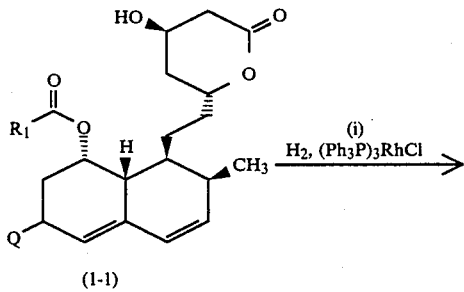

(1-1)

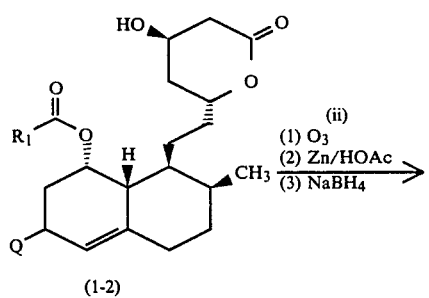

(1-2)

-continued
SCHEME 1

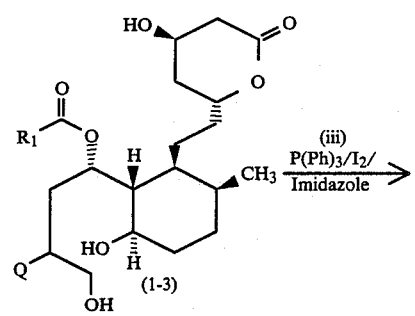

(1-3)

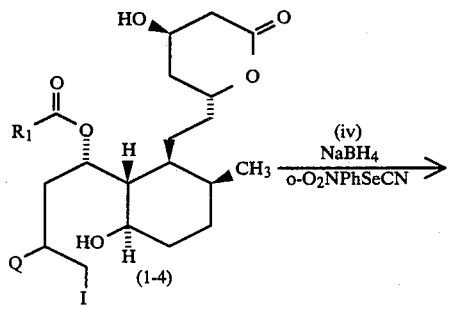

(1-4)

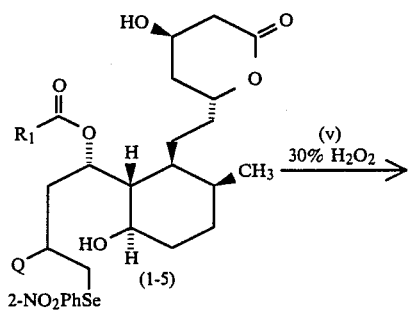

(1-5)

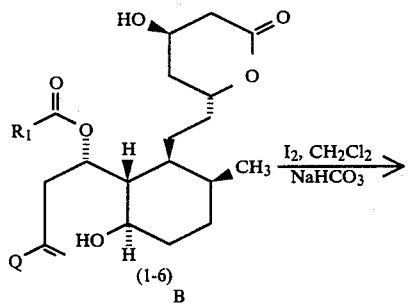

(1-6)

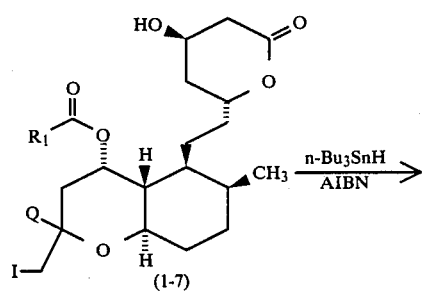

(1-7)

SCHEME 1
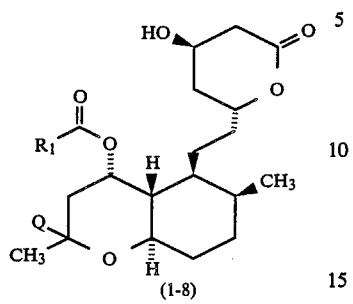
(1-8)
Q is CH₃, CH₂OT or H.
T is a hydroxyl protecting group or H.
SCHEME 2
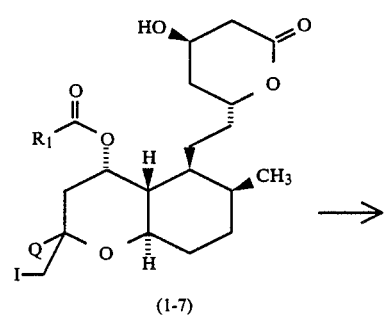
(1-7)
→
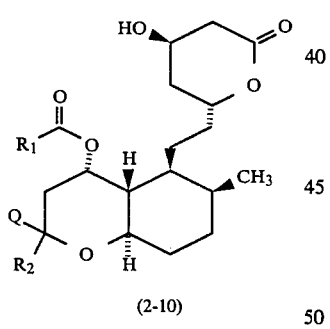
(2-10)
SCHEME 2A
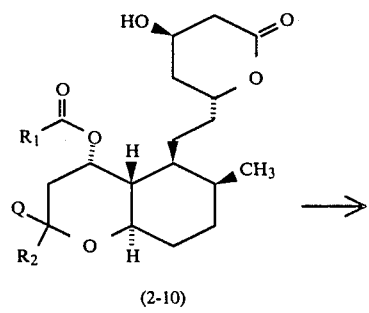
(2-10)
→
SCHEME 2A -continued
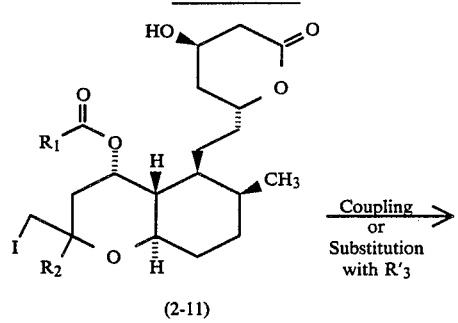
(2-11)
$\xrightarrow{\text{Coupling or Substitution with } R'_3}$
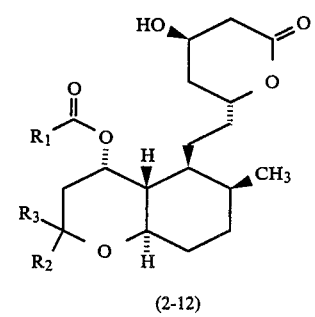
(2-12)
SCHEME 3
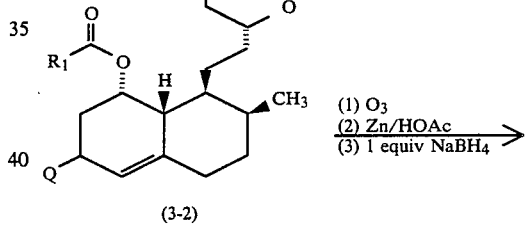
(3-2) $\xrightarrow{\text{(1) O}_3 \text{ (2) Zn/HOAc (3) 1 equiv NaBH}_4}$
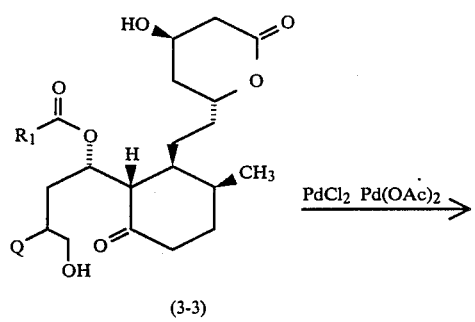
(3-3) $\xrightarrow{\text{PdCl}_2 \text{ Pd(OAc)}_2}$
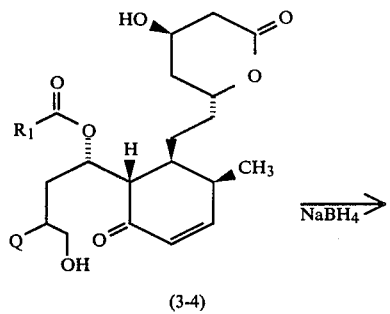
(3-4) $\xrightarrow{\text{NaBH}_4}$

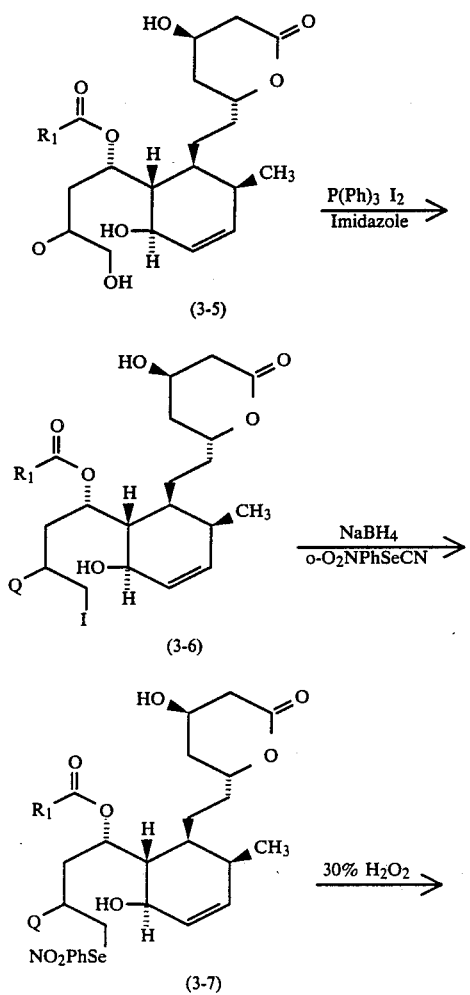
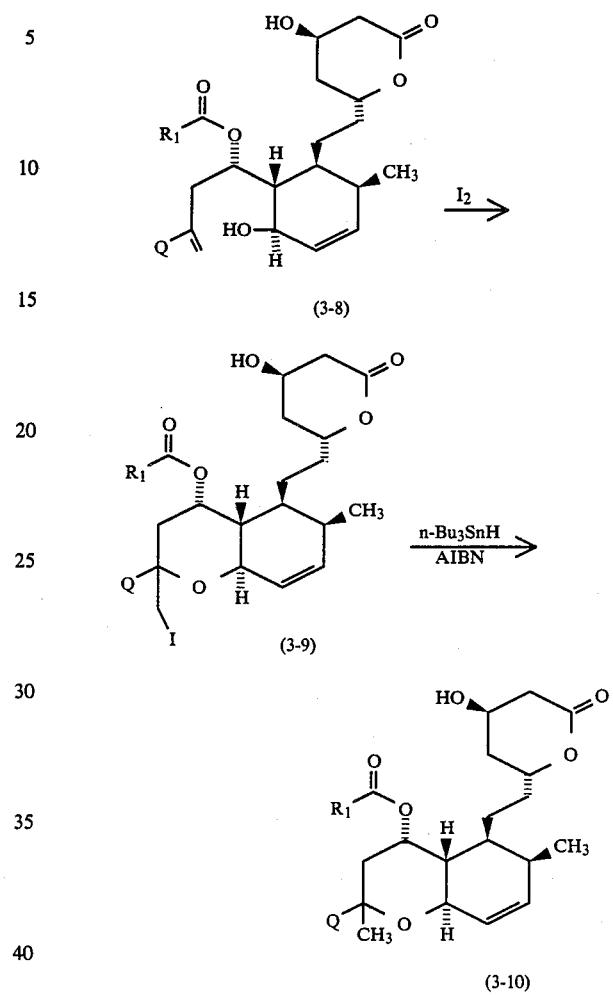
SCHEME 4
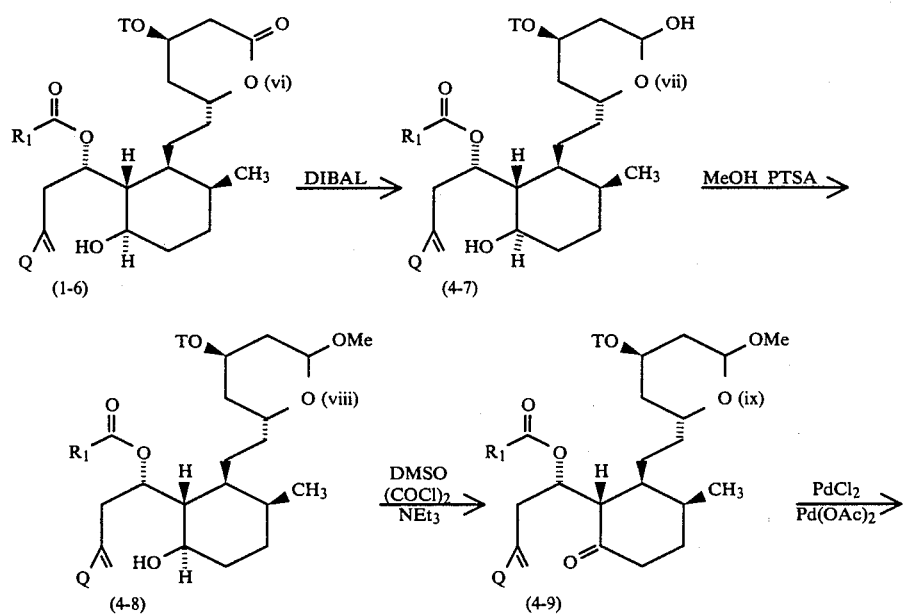

SCHEME 4
-continued
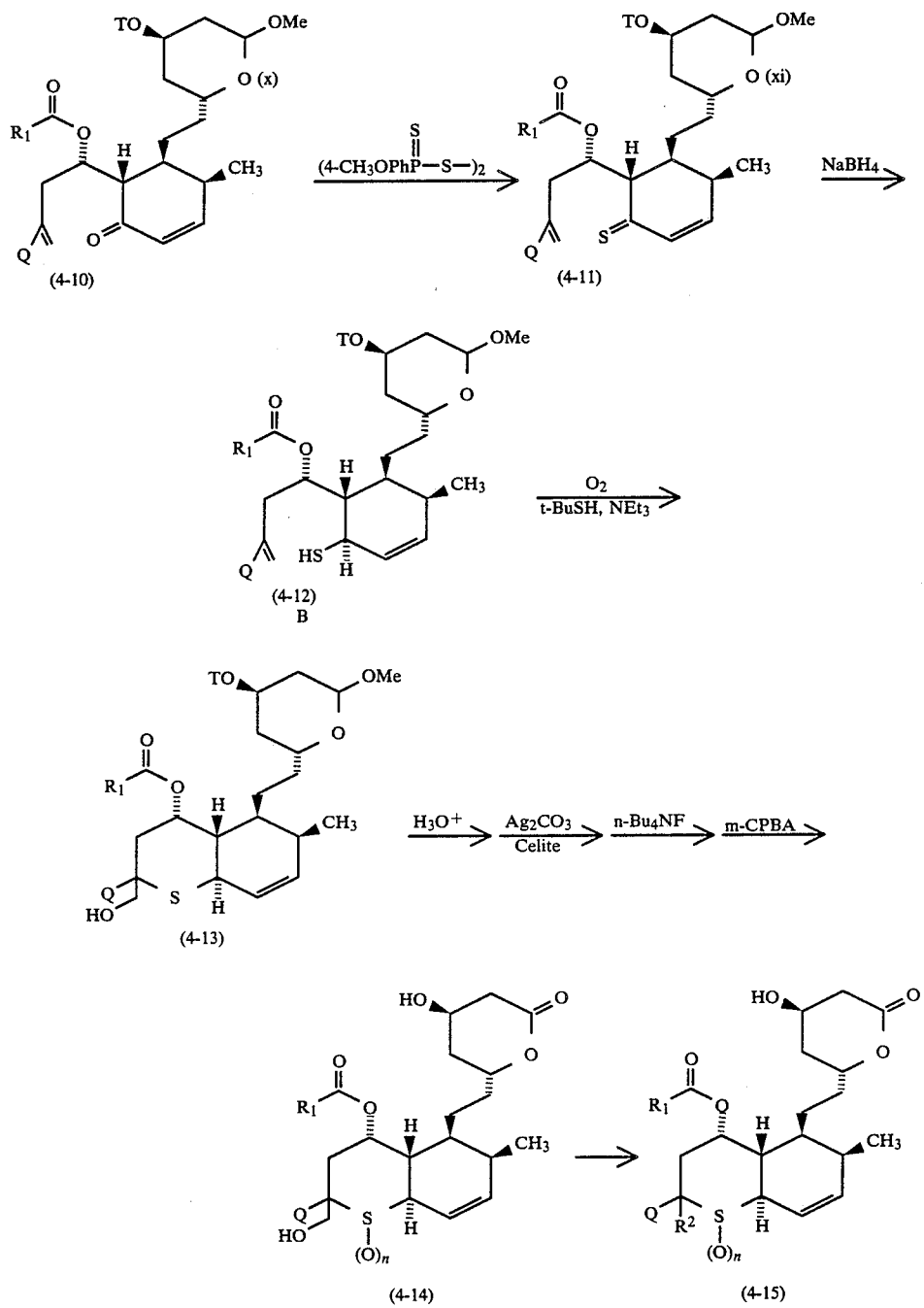
(4-10) → (4-11) → (4-12) B → (4-13) → (4-14) → (4-15)
T is a hydroxyl protecting group such as tert-butyldiphenylsilyl

SCHEME 4A
SCHEME 5
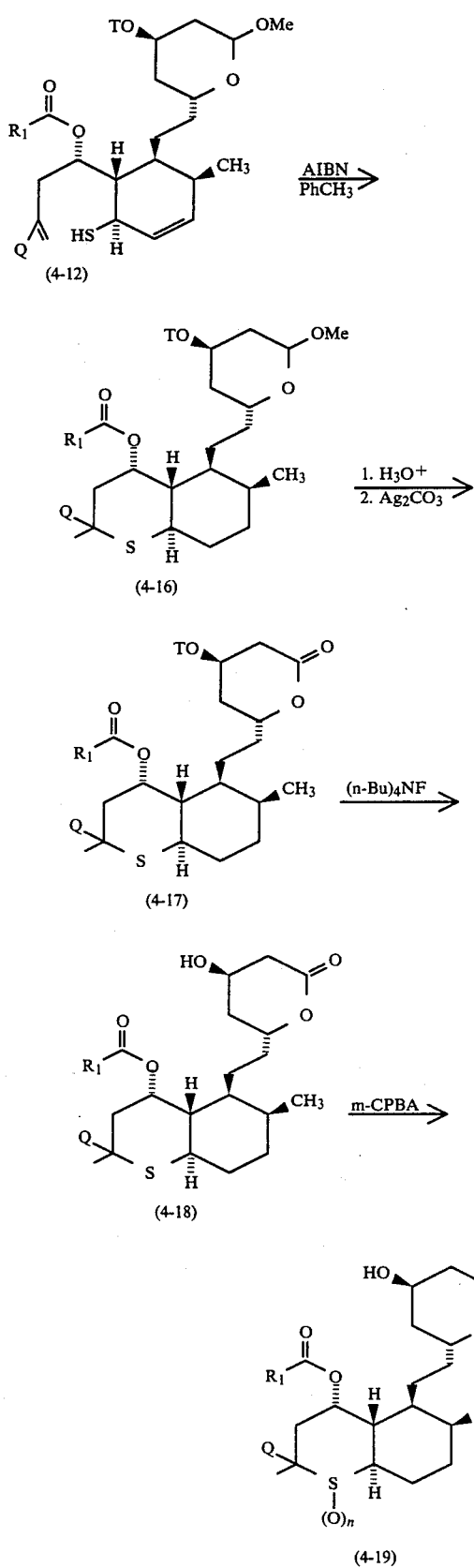
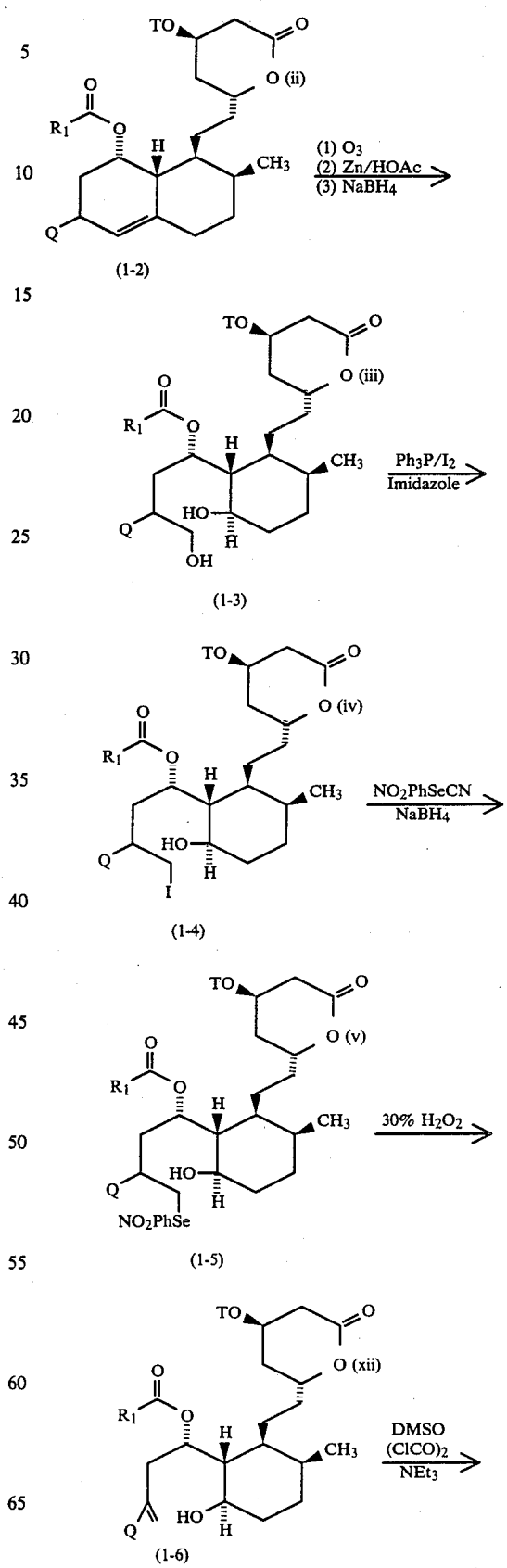

-continued
SCHEME 5

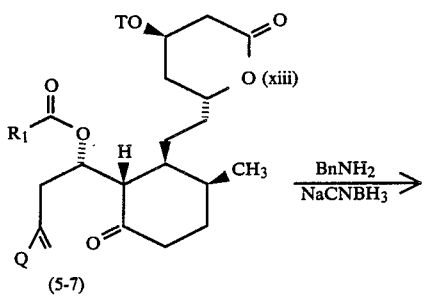

(5-7)

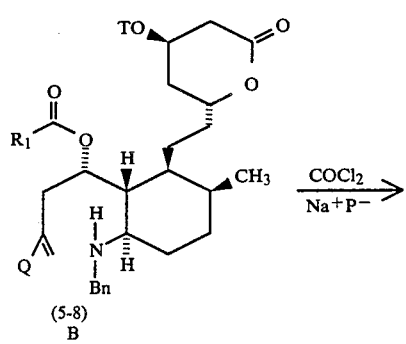

(5-8)
B

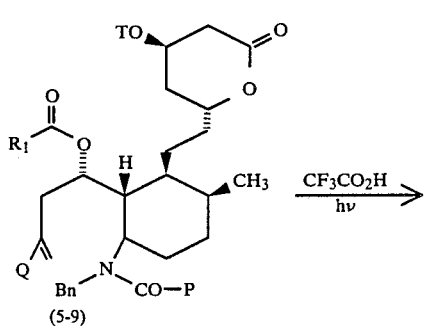

(5-9)

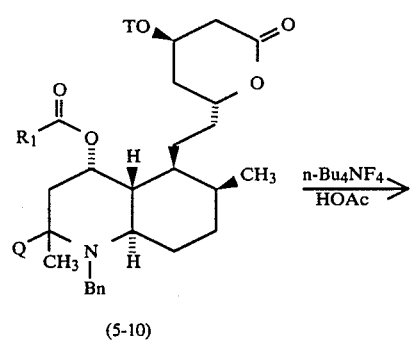

(5-10)

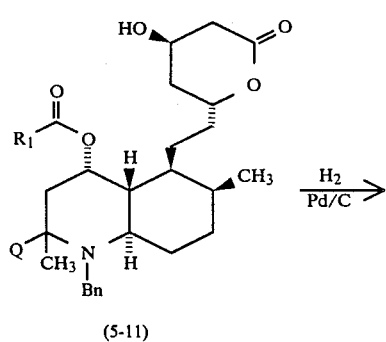

(5-11)

-continued
SCHEME 5

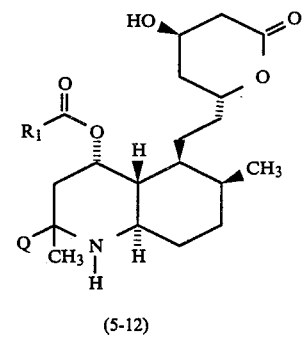

(5-12)

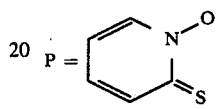

T is a hydroxy protecting group such as diphenyltert-butylsilyl

Bn = benzyl

Except where specifically defined to the contrary the terms "alkyl", "alkoxy" and "acyl" include both the straight-chain and branched-chain species of the term.

One embodiment of this invention is the intermediate compounds of formula (B):

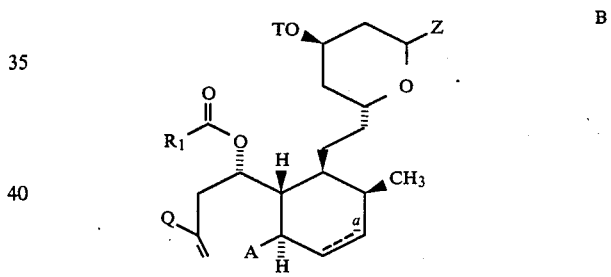

wherein:
A is HO, or SH;
Q is $CH_3$, $CH_2OT$, or H;
T is H, tert-butyldimethylsilyl, tert-butyldiphenylsilyl, trimethylsilyl, triethylsilyl, triisopropylsilyl or tetrahydropyranyl;
Z is $OCH_3$, or Z together with the carbon to which it is attached represents C=O;
$R_1$ is selected from:
(1) $C_{1-10}$ alkyl;
(2) substituted $C_{1-10}$ alkyl in which one or more substituent(s) is selected from
  (a) halogen,
  (b) hydroxy,
  (c) $C_{1-10}$ alkoxy,
  (d) $C_{1-5}$ alkoxycarbonyl,
  (e) $C_{1-5}$ acyloxy,
  (f) $C_{3-8}$ cycloalkyl,
  (g) phenyl,
  (h) substituted phenyl in which the substituents are X and Y,
  (i) $C_{1-10}$ alkylS(O)$_n$ in which n is 0 to 2,
  (j) $C_{3-8}$ cycloalkylS(O)$_n$,
  (k) phenylS(O)$_n$, (l) substituted phenylS(O)$_n$ in which the substituents are X and Y, and
(m) oxo;
(3) C$_{1-10}$ alkoxy;
(4) C$_{2-10}$ alkenyl;
(5) C$_{3-8}$ cycloalkyl;
(6) substituted C$_{3-8}$ cycloalkyl in which one substituent is selected from
  (a) C$_{1-10}$ alkyl,
  (b) substituted C$_{1-10}$ alkyl in which the substituent is selected from
    (i) halogen,
    (ii) hydroxy,
    (iii) C$_{1-10}$ alkoxy,
    (iv) C$_{1-5}$ alkoxycarbonyl,
    (v) C$_{1-5}$ acyloxy,
    (vi) phenyl,
    (vii) substituted phenyl in which the substituents are X and Y,
    (viii) C$_{1-10}$ alkylS(O)$_n$,
    (ix) C$_{3-8}$ cycloalkylS(O)$_n$,
    (x) phenylS(O)$_n$,
    (xi) substituted phenylS(O)$_n$ in which the substituents are X and Y, and
    (xii) oxo,
  (c) C$_{1-10}$ alkylS(O)$_n$,
  (d) C$_{3-8}$ cycloalkylS(O)$_n$,
  (e) phenylS(O)$_n$,
  (f) substituted phenylS(O)$_n$ in which the substituents are X and Y,
  (g) halogen,
  (h) hydroxy,
  (i) C$_{1-10}$ alkoxy,
  (j) C$_{1-5}$ alkoxycarbonyl,
  (k) C$_{1-5}$ acyloxy,
  (l) phenyl, and
  (m) substituted phenyl in which the substituents are X and Y;
(7) phenyl;
(8) substituted phenyl in which the substituents are X and Y;
(9) amino;
(10) C$_{1-5}$ alkylamino;
(11) di(C$_{1-5}$ alkyl)amino;
(12) phenylamino;
(13) substituted phenylamino in which the substituents are X and Y;
(14) phenyl C$_{1-10}$ alkylamino;
(15) substituted phenyl C$_{1-10}$ alkylamino in which the substituents are X and Y;
(16) a member selected from
  (a) piperidinyl,
  (b) pyrrolidinyl,
  (c) piperazinyl,
  (d) morpholinyl, and
  (e) thiomorpholinyl; and
(17) R$_5$S in which R$_5$ is selected from
  (a) C$_{1-10}$ alkyl,
  (b) phenyl, and
  (c) substituted phenyl in which the substituents are X and Y;

X and Y independently are hydrogen, halogen, trifluoromethyl, C$_{1-3}$ alkyl, nitro, cyano or group selected from:
(1) R$_6$O(CH$_2$)$_m$ in which m is 0 to 3 and R$_6$ is hydrogen, C$_{1-3}$alkyl or hydroxy-C$_{2-3}$alkyl;
(2)

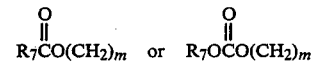

in which R$_7$ is hydrogen, C$_{1-3}$alkyl, hydroxy-C$_{2-3}$alkyl, phenyl, naphthyl, amino-C$_{1-3}$alkyl, C$_{1-3}$alkylamino-C$_{1-3}$alkyl, di(C$_{1-3}$alkyl)amino-C$_{1-3}$alkyl, hydroxy-C$_{2-3}$ alkylamino-C$_{1-3}$alkyl or di(hydroxy-C$_{2-3}$alkyl) amino-C$_{1-3}$alkyl; provided that in

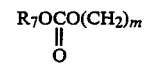

R$_7$ is not H;
(3)

in which R$_8$ is hydrogen, C$_{1-3}$alkyl, hydroxy-C$_{2-3}$ alkyl, C$_{1-3}$alkoxy-C$_{1-3}$alkyl, phenyl or naphthyl;
(4)

R$_9$R$_{10}$N(CH$_2$)$_m$, R$_9$R$_{10}$NC(CH$_2$)$_m$ or

in which R$_9$ and R$_{10}$ independently are hydrogen, C$_{1-3}$ alkyl, hydroxy-C$_{2-3}$alkyl or R$_9$ and R$_{10}$ together with the nitrogen atom to which they are attached form a heterocyclic group selected from piperidinyl, pyrrolidinyl, piperazinyl, morpholinyl or thiomorpholinyl;
(5) R$_{11}$S(O)$_n$(CH$_2$)$_m$ in which R$_{11}$ is hydrogen, C$_{1-3}$alkyl, amino, C$_{1-3}$alkylamino or di(C$_{1-3}$alkyl)amino;

a is a single bond or a double bond; halogen is F or Cl; n is 0 to 2.

In one class of this embodiment are compounds (B) where R$_1$ is selected from:
(1) C$_{1-10}$ alkyl;
(2) substituted C$_{1-10}$ alkyl in which one or more substituent(s) is selected from
  (a) halogen,
  (b) hydroxy,
  (c) C$_{1-10}$ alkoxy,
  (d) C$_{1-5}$ alkoxycarbonyl,
  (e) C$_{1-5}$ acyloxy,
  (f) C$_{3-8}$ cycloalkyl,
  (g) phenyl,
  (h) substituted phenyl in which the substituents are X and Y, and
  (i) oxo;
(3) C$_{3-8}$ cycloalkyl;
(4) substituted C$_{3-8}$ cycloalkyl in which one substituent is selected from
  (a) C$_{1-10}$ alkyl,
  (b) substituted C$_{1-10}$ alkyl in which the substituent is selected from
    (i) halogen,
    (ii) hydroxy, (iii) C$_{1-10}$ alkoxy,
(iv) C$_{1-5}$ acyloxy,
(v) C$_{1-5}$ alkoxycarbonyl,
(vi) phenyl,
(vii) substituted phenyl in which the substituents are X and Y, and
(viii) oxo,
(c) halogen,
(d) hydroxy,
(e) C$_{1-10}$ alkoxy,
(f) C$_{1-5}$ alkoxycarbonyl,
(g) C$_{1-5}$ acyloxy,
(h) phenyl,
(i) substituted phenyl in which the substituents are X and Y;
(5) phenylamino;
(6) substituted phenylamino in which the substituents are X and Y;
(7) phenyl C$_{1-10}$ alkylamino; and
(8) substituted phenyl C$_{1-10}$ alkylamino in which the substituents are X and Y.

In a subclass are those compounds of formula (B) wherein:
R$_1$ is selected from:
(1) C$_{1-10}$ alkyl;
(2) C$_{3-8}$ cycloalkyl;
(3) phenylamino; and
(4) substituted phenylamino in which the substituents are X and Y.

Illustrative of this subclass are those compounds of formula (B) wherein:
R$_1$ is C$_{1-10}$ alkyl;
Q is CH$_3$; and
a is a single bond.

Further illustrating this subclass are those compounds of formula (B) wherein:
T is tert-butyldimethylsilyl;
R$_1$ is 2-methyl-2-butyl or 2-butyl.

Exemplifying this illustration are those compounds of formula (B) selected from the group wherein:
(1) R$_1$ is 2-methyl-2-butyl, A is OH, Z is C=O;
(2) R$_1$ is 2-butyl, A is OH, Z is C=O;
(3) R$_1$ is 2-methyl-2-butyl, A is SH, Z is OCH$_3$;
(4) R$_1$ is 2-butyl, A is SH, Z is OCH$_3$.

In a second embodiment are the compounds of formula (B):

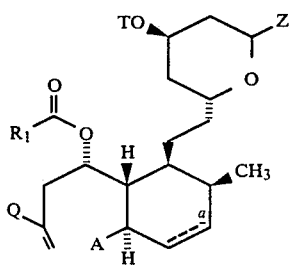

B wherein:
A is HN—R$_N$;
Q is CH$_3$, CH$_2$OT, or H;
T is H, tert-butyldimethylsilyl, tert-butyldiphenylsilyl, trimethylsilyl, triethylsilyl, triisopropylsilyl or tetrahydropyranyl;
Z together with the carbon to which it is attached is C=O;
R$_1$ is selected from:

(1) C$_{1-10}$ alkyl;
(2) substituted C$_{1-10}$ alkyl in which one or more substituent(s) is selected from
(a) halogen,
(b) hydroxy,
(c) C$_{1-10}$ alkoxy,
(d) C$_{1-5}$ alkoxycarbonyl,
(e) C$_{1-5}$ acyloxy,
(f) C$_{3-8}$ cycloalkyl,
(g) phenyl,
(h) substituted phenyl in which the substituents are X and Y,
(i) C$_{1-10}$ alkylS(O)$_n$ in which n is 0 to 2,
(j) C$_{3-8}$ cycloalkylS(O)$_n$,
(k) phenylS(O)$_n$,
(l) substituted phenylS(O)$_n$ in which the substituents are X and Y, and
(m) oxo;
(3) C$_{1-10}$ alkoxy;
(4) C$_{2-10}$ alkenyl;
(5) C$_{3-8}$ cycloalkyl;
(6) substituted C$_{3-8}$ cycloalkyl in which one substituent is selected from
(a) C$_{1-10}$ alkyl,
(b) substituted C$_{1-10}$ alkyl in which the substituent is selected from
(i) halogen,
(ii) hydroxy,
(iii) C$_{1-10}$ alkoxy,
(iv) C$_{1-5}$ alkoxycarbonyl,
(v) C$_{1-5}$ acyloxy,
(vi) phenyl,
(vii) substituted phenyl in which the substituents are X and Y
(viii) C$_{1-10}$ alkylS(O)$_n$,
(ix) C$_{3-8}$ cycloalkyl(S(O)$_n$,
(x) phenylS(O)$_n$,
(xi) substituted phenylS(O)$_n$ in which the substituents are X and Y, and
(xii) oxo,
(c) C$_{1-10}$ alkylS(O)$_n$,
(d) C$_{3-8}$ cycloalkylS(O)$_n$,
(e) phenylS(O)$_n$,
(f) substituted phenylS(O)$_n$ in which the substituents are X and Y,
(g) halogen,
(h) hydroxy,
(i) C$_{1-10}$ alkoxy,
(j) C$_{1-5}$ alkoxycarbonyl,
(k) C$_{1-5}$ acyloxy,
(l) phenyl, and
(m) substituted phenyl in which the substituents are X and Y;
(7) phenyl;
(8) substituted phenyl in which the substituents are X and Y;
(9) amino;
(10) C$_{1-5}$ alkylamino;
(11) di(C$_{1-5}$ alkyl)amino;
(12) phenylamino;
(13) substituted phenylamino in which the substituents are X and Y;
(14) phenyl C$_{1-10}$ alkylamino;
(15) substituted phenyl C$_{1-10}$ alkylamino in which the substituents are X and Y;
(16) a member selected from
(a) piperidinyl,
(b) pyrrolidinyl, (c) piperazinyl,
(d) morpholinyl, and
(e) thiomorpholinyl; and
(17) $R_5S$ in which $R_5$ is selected from
  (a) $C_{1-10}$ alkyl,
  (b) phenyl, and
  (c) substituted phenyl in which the substituents are X and Y;

$R_N$ is selected from:
  (a) $C_{1-5}$ alkyl;
  (b) phenyl $C_{1-5}$ alkyl;

X and Y independently are hydrogen, halogen, trifluoromethyl, $C_{1-3}$ alkyl, nitro, cyano or group selected from:
(1) $R_6O(CH_2)_m$ in which m is 0 to 3 and $R_6$ is hydrogen, $C_{1-3}$ alkyl or hydroxy-$C_{2-3}$ alkyl;
(2)

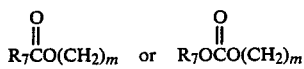

in which $R_7$ is hydrogen, $C_{1-3}$ alkyl, hydroxy-$C_{2-3}$ alkyl, phenyl, naphthyl, amino-$C_{1-3}$ alkyl, $C_{1-3}$ alkylamino-$C_{1-3}$ alkyl, di($C_{1-3}$ alkyl)amino-$C_{1-3}$ alkyl, hydroxy-$C_{2-3}$ alkylamino-$C_{1-3}$ alkyl or di(hydroxy-$C_{2-3}$ alkyl) amino-$C_{1-3}$ alkyl; provided that in

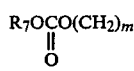

$R_7$ is not H;
(3)

in which $R_8$ is hydrogen, $C_{1-3}$ alkyl, hydroxy-$C_{2-3}$ alkyl, $C_{1-3}$ alkoxy-$C_{1-3}$ alkyl, phenyl or naphthyl;
(4)

 

in which $R_9$ and $R_{10}$ independently are hydrogen, $C_{1-3}$ alkyl, hydroxy-$C_{2-3}$ alkyl or $R_9$ and $R_{10}$ together with the nitrogen atom to which they are attached form a heterocyclic group selected from piperidinyl, pyrrolidinyl, piperazinyl, morpholinyl or thiomorpholinyl;
(5) $R_{11}S(O)_n(CH_2)_m$ in which $R_{11}$ is hydrogen, $C_{1-3}$ alkyl, amino, $C_{1-3}$ alkylamino or di($C_{1-3}$ alkyl)amino;

a is a single bond or a double bond; halogen is F or Cl; n is 0 to 2.

In one class of this embodiment are compounds (B) wherein $R_1$ is selected from:
(1) $C_{1-10}$ alkyl;
(2) substituted $C_{1-10}$ alkyl in which one or more substituent(s) is selected from
  (a) halogen,
  (b) hydroxy,
  (c) $C_{1-10}$ alkoxy,
  (d) $C_{1-5}$ alkoxycarbonyl,
  (e) $C_{1-5}$ acyloxy,
  (f) $C_{3-8}$ cycloalkyl,
  (g) phenyl,
  (h) substituted phenyl in which the substituents are X and Y, and
  (i) oxo;
(3) $C_{3-8}$ cycloalkyl;
(4) substituted $C_{3-8}$ cycloalkyl in which one substituent is selected from
  (a) $C_{1-10}$ alkyl,
  (b) substituted $C_{1-10}$ alkyl in which the substituent is selected from
    (i) halogen,
    (ii) hydroxy,
    (iii) $C_{1-10}$ alkoxy,
    (iv) $C_{1-5}$ acyloxy,
    (v) $C_{1-5}$ alkoxycarbonyl,
    (vi) phenyl,
    (vii) substituted phenyl in which the substituents are X and Y, and
    (viii) oxo,
  (c) halogen,
  (d) hydroxy,
  (e) $C_{1-10}$ alkoxy,
  (f) $C_{1-5}$ alkoxycarbonyl,
  (g) $C_{1-5}$ acyloxy,
  (h) phenyl,
  (i) substituted phenyl in which the substituents are X and Y;
(5) phenylamino;
(6) substituted phenylamino in which the substituents are X and Y;
(7) phenyl $C_{1-10}$ alkylamino; and
(8) substituted phenyl $C_{1-10}$ alkylamino in which the substituents are X and Y.

In a subclass are those compounds of formula (B) wherein:
$R_1$ is selected from:
(1) $C_{1-10}$ alkyl;
(2) $C_{3-8}$ cycloalkyl;
(3) phenylamino; and
(4) substituted phenylamino in which the substituents are X and Y.

Illustrative of this subclass are those compounds of formula (B) wherein:
$R_1$ is $C_{1-10}$ alkyl;
Q is $CH_3$; and
a is a single bond.

Further illustrating this subclass are those compounds of formula (B) wherein:
T is tert-butyldimethylsilyl;
$R_1$ is 2-methyl-2-butyl or 2-butyl.
$R_N$ is phenyl$CH_2$—.

Exemplifying this illustration are those compounds of formula (B) selected from the group wherein:
(1) $R_1$ is 2-methyl-2-butyl;
(2) $R_1$ is 2-butyl.

A third embodiment of the present invention is a process for the preparation of intermediates of formula (B) from a starting material of formula (1—1) such as lovastatin.

In one class of this embodiment is the process for preparing intermediates of formula (B) wherein A is OH. This process is outlined in scheme 1 wherein a is a single bond, and in scheme 3 wherein a is a double bond.

In a second class is the process wherein intermediates prepared are of formula (B) wherein A is SH. This process is outlined in scheme 4.

In a third class the intermediates prepared are of formula (B) wherein A is HN—R$_N$. This process is outlined in scheme 5.

Intermediates of formula (B) wherein A is OH and a is a single bond are prepared in a process which comprises:

(i) Treating the compound (1—1)

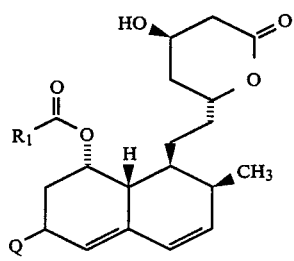

(1-1)

wherein R$_1$, and Q are defined above, with a tris(-triarylphosphine) rhodium halide in the presence of hydrogen to form a compound of formula (1-2);

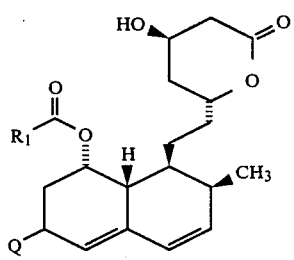

(1-2)

(ii) Treating compound (1-2) with ozone in an alcoholic solvent followed by reduction of the ozonide with zinc/acetic acid and reduction of the intermediate ketoaldehyde with sodium borohydride to yield compound (1-3);

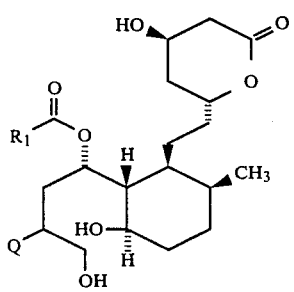

(1-3)

(iii) Contacting compound (1-3) with an iodinating reagent such as iodine/triphenylphosphine/imidazole to form compound (1-4);

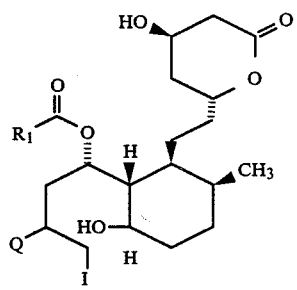

(1-4)

(iv) Treating compound (1-4) with a 2-nitrophenyl selenocyanate and NaBH$_4$ to yield a compound (1-5);

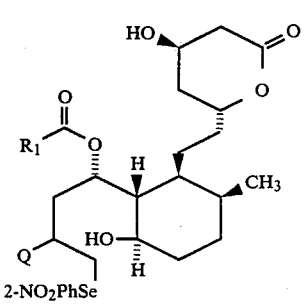

(1-5)

(v) Treating compound (1-5) with H$_2$O$_2$/THF to yield compound (1-6);

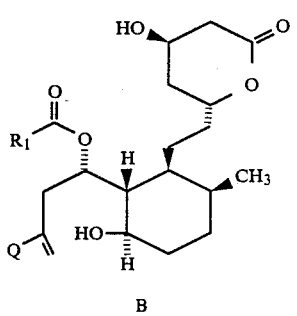

(1-6)

B

Intermediates of formula (B) wherein a is a double bond can be prepared by a variation on the above sequence as shown in scheme 3. The ketoaldehyde formed in step (ii) is isolated and reduced with one equivalent of sodium borohydride to yield a ketoalcohol (3—3);

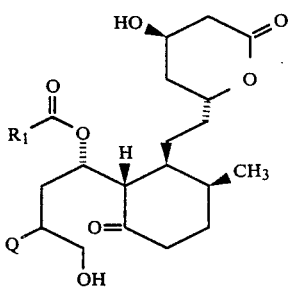

(3-3)

followed by treatment of compound (3—3) with a dehydrogenating agent such as PdCl$_2$/Pd(OAc)$_2$ to yield the unsaturated ketoalcohol (3-4);

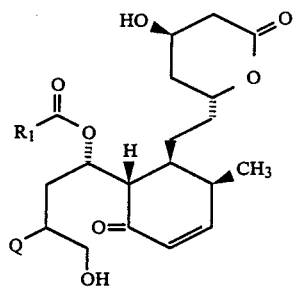
(3-4)

then treatment of compound (3-4) with a reducing agent such as sodium borohydride to yield compound (3-5).

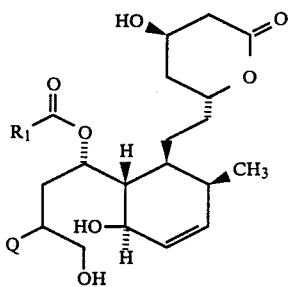
(3-5)

Compound (3-5) is the unsaturated analog of compound (1-3) and can be converted to a compound of formula (B) following the steps (iii), (iv), and (v) as described above.

Intermediates of formula (B) wherein A is SH are prepared in a sequence comprising steps (i)→(v) as described above and further comprising:

(vi) Contacting compound (1-6) with diisobutylaluminum hydride (dibal) to yield compound (4-7);

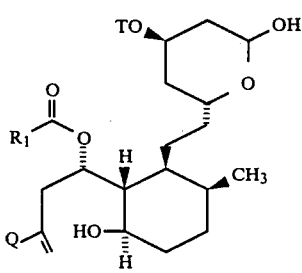
(4-7)

(vii) treating compound (4-7) with methanol and para-toluenesulfonic acid (pTSA) to yield compound (4-8);

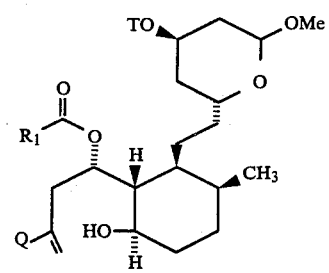
(4-8)

(viii) treating compound (4-8) with (COCl)$_2$ and dimethylsulfoxide (DMSO) and a base such as triethylamine to yield compound (4-9);

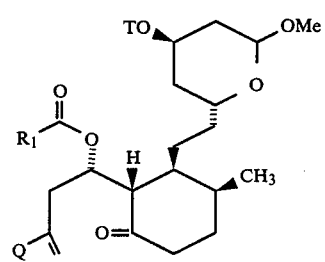
(4-9)

(ix) treating compound (4-9) with a dehydrogenating agent such as PdCl$_2$/Pd(OAc)$_2$ to yield the eneone compound (4-10);

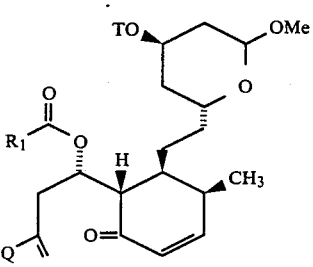
(4-10)

(x) treating compound (4-10) with 2,4-bis(4-methoxyphenyl)-1,3,2,4-dithiadiphosphetane-2,4-disulfide to yield the thione (4-11);

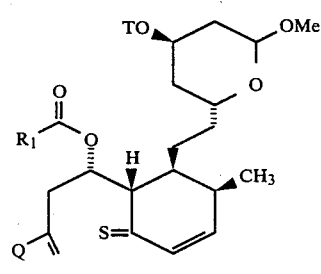
(4-11)

(xi) treating compound (4-11) with a thione reducing agent such as NaBH$_4$ to yield the intermediate (B) (4-12);

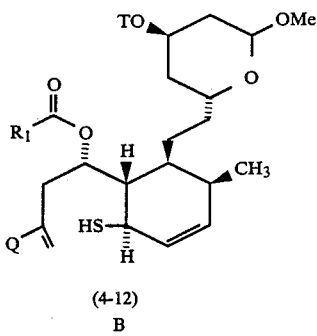

(4-12)
B

Where the double bond in the 3,4 position of compound (4-12) is not desired, step (ix) is omitted from the above sequence and compound (4-9) is treated as in step (x).

Intermediates of formula (B) wherein A is $HNR_N$ and a is a single bond are prepared as shown in Scheme 5 in a sequence comprising steps (i)→(v), as outlined above for compound (1-6), and further comprising:

(xii) treating compound (1-6) with $(ClCO)_2$ in DMSO and a base such as triethylamine to yield compound (5-7);

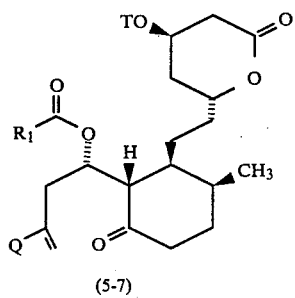

(5-7)

(xiii) contacting compound (5-7) with $R_N NH_2$, an alkyl or arylalkylamine such as benzylamine and $NaCNBH_3$ to yield an intermediate (B) (5-8);

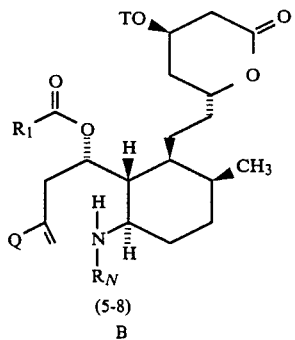

(5-8)
B

Intermediates of formula B wherein A is $HNR_N$ and a is a double bond are prepared in a sequence comprising steps (i)→(v) and step (xii) as discussed above for scheme 5 and further comprising:

(xiiia) treating compound (5-7) with $PdCl_2/Pd(OAc)_2$ to yield compound (5-7a) wherein a is a double bond, followed by step (xiii) to yield compound (B) (5-8a).

Compound (1—1) may be prepared from lovastatin or mevastatin by replacement, if necessary, of the 2-methylbutyryl moiety by $R_1CO$. The hydrolysis of the 8-acyloxy moiety and reesterification may be accomplished following the procedure in U.S. Pat. No. 4,444,784. The conversion to compounds (1—1) wherein Q is $CH_2OH$ and its silyl protected form can be carried out following the procedures in U.S. patent application Ser. Nos. 161530, 161579, 161529 all filed on Feb. 29, 1988.

In step (i) of Scheme 1 the 3,4-double bond is hydrogenated employing the procedure described in copending U.S. application 092,804 filed Sept. 13, 1987. Alternatively the procedure described in U.S. Pat. No. 4,351,844 and J. Org. Chem., 48, 1991 (1983) may also be used.

In step (ii) the monoene (1-2) is treated with ozone in an alcoholic solvent, such as methanol, at about −78° C. followed by reduction of the ozonide with Zn/acetic acid or triphenylphosphine and reduction of the intermedidate ketoaldehyde with a borohydride reducing agent such as $NaBH_4$ or $BH_3 \cdot THF$.

The primary alcohol moiety of compound (1-3) is converted to the halide with a halogenating reagent such as iodine/triphenylphosphine/imidazole. Alternatively the alcohol could be converted to the tosylate by reaction with tosyl chloride. The tosyl moiety in turn could be replaced by a halide by a standard substitution with an alkali metal halide such as NaI in acetone.

In step (iv) the halide is replaced by phenylselenium by employment of a selenating reagent such as o—$NO_2PhSeCN$ and $NaBH_4$. Alternatively one could employ groups such as phenylsulfides which could undergo oxidative elimination in step (v).

Compound (1-5) undergoes oxidative elimination in step (v) using 30% $H_2O_2$ in tetrahydrofuran (THF) at about 25° C., to yield intermediate (1-6).

Intermediate (1-6) may be converted to products (I) and (II) following the outline in schemes 1,2 and 3 and the details in copending application Ser. No. 212,767 filed June 29, 1988.

In scheme 4 the lactone moiety of compound (1-6) is protected as an acetal by the reaction of (1-6) with diisobutyl aluminum hydride (dibal) followed by reaction with an alcohol such as methanol with an acid catalyst such as para-toluene sulfonic acid (pTSA).

In step (viii) the 4a-alcohol is converted to the ketone via a Swern oxidation.

A double bond may be inserted in the 3,4-positions of compound (4-9) by a $PdCl_2/Pd(OAc)_2$ catalyzed dehydrogenation (step ix) to form compound (4-10).

The 4a-keto moiety of compound (4-9) or compound (4-10) may be converted (step x) to a thioketone (4-10) by use of 2,4-bis(4-methoxyphenyl)-1,3,2,4-dithiadiphosphetane-2,4-disulfide employing the procedures of Pederson et al., Bull. Soc. chem. Belg., 87, 223, (1978).

In step (xi) the thioketone is reduced with a borohydride reducing agent, such as $NaBH_4$, to yield intermediate (4-12).

Intermediates (4-12) may be converted to products I and II following the outline in schemes 4 and 4a and the detailed description in copending application Ser. No. 212,767 filed June 29, 1988.

In step (xii) of scheme 5 the 4a-alcohol of compound (5-6) is converted to the ketone via a Swern oxidation.

Step (xiii) of scheme 5 employs a reductive amination of compound (5-7) with an alkyl or arylalkylamine such as benzylamine ($BnNH_2$), to yield intermediate (5-8).

Intermediates (5–8) may be converted to products I and II following the outline in scheme 5 and the detailed description in copending application Ser. No. 212,767 filed June 29, 1988. If desired, the 3,4-double bond can be inserted by reaction of compound (5–7) with PdCl$_2$/Pd(OAc)$_2$ folowing an analogous methodology to that expressed in scheme 4. The enone product is then transformed further to compound (5–8a) etc. following the outline of scheme 5.

The following examples illustrate the preparation of compounds (B) and the compounds of formulae (I) and (II) and as such are not to be considered as limiting the invention set forth in the Claims appended hereto.

EXAMPLE 1

Preparation of
6(R)-[2-[8(S)-(2,2-dimethylbutyryloxy-2(S)-methyl-5-oxa-6,6-dimethyl-1,2,3,4,4a(R),7,8,8a(R)-octahydronaphthyl-1(S)ethyl]-4(R)-hydroxy-3,4,5,6-tetrahydro-2H-pyran-2-one.

Step 1: Preparation of
6(R)-[2-(8(S)-(2,2-dimethyl-butyryloxy)-2(S)-methyl-6(R)-methyl-1,2,3,4,6,7,8,8a(S)-octahydronaphthyl-1(S)ethyl]-4(R)-hydroxy-3,4,5,6-tetrahydro-2H-pyran-2-one (2).

Nitrogen was bubbled through a solution of 50% toluene in absolute ethanol (300 mL) for 5 minutes. Wilkinson's catalyst (5.0 g, 33%/wt.) was added to the solvent and the mixture reduced at room temperature under 50 psi H$_2$ for 1 hour. Simvastatin (1) (15 g, 36 mmol) was added and the resulting pale yellow solution reduced at room temperature under H$_2$ (60 psi) for 40 hours. The mixture was concentrated and the residue heated in toluene (700 mL) at 60° C. in the presence of thiourea (5.0 g, 64 mmol) for 1.5 hours. The mixture was cooled to 0° C. (ice bath), filtered, and concentrated. The residue was diluted with 50% EtOAc/hexane and passed through a pad of silica (~250 cc) to give 2 as a beige solid; mp=128°–129° C. (ethyl acetate/hexane); TLC R$_f$=0.65 (EtOAc); $^1$NMR* (CDCl$_3$)δ5.36 (bs, 1H), 5.30 (m,1H), 4.58 (m,1H), 4.33 (m,1H), 2.68 (dd,J=17 and 5Hz,1H), 2.68 (m,1H), 2.59 (dd, J=17 and 4Hz,1H), 2.30–1.20 (m), 1.13 (s,3H), 1.12 (s,3H), 1.05 (d, J-7Hz,3H), 0.87 (d, J=7Hz,3H), 0.82 (t, J=7Hz,3H).

*NMR spectra were recorded on a Varion Xl-300 spectrometer.

Step 2: Preparation of
6(R)-[2-[6(R)-(1(S)-2,2-dimethylbutyryloxy-3(R)-methyl-butan-4-ol)-2(S)-methyl-5(R)-hydroxy-cyclohexyl-1(S)]ethyl]-4(R)-hydroxy-3,4,5,6-tetrahydro-2H-pyran-2-one (3).

Ozone was passed through a red solution of monoene 2 (420 mg, 1.0 mmol) and 1-(p-phenylazophenylazo)-2-naphthol (sudan III) (5 mg) in CH$_3$OH (10 mL) at −78° C. until the red color dissipated (10 minutes. Argon was then bubbled through the solution to remove excess ozone. Addition of zinc (200 mg, 3.0 mmol) and acetic acid (1.0 mL) was followed by removal of the cooling bath and vigorous stirring for 15 minutes. The reaction mixture was diluted with ethyl acetate and filtered through celite. The filtrate was washed with H$_2$O and brine, dried (MgSO$_4$), and concentrated. The crude keto-aldehyde was immediately dissolved in THF/H$_2$O (10:1, 8.0 mL), cooled to 0° C., and treated with NaBH$_4$ (100 mg, 3.0 mmol) in 2 portions. After 20 minutes the reaction mixture was diluted with ethyl acetate, washed with H$_2$O, and brine, dried (MgSO$_4$), and concentrated.

Flash chromatography (silica, EtOAc) gave the desired product as an oil.

$^1$H NMR (CDCl$_3$): δ5.55 (m, 1H), 4.72 (m, 1H), 4.38 (m, 1H), 3.61 (dd, 1H, J=10 and 3Hz), 3.44 (dd, 1H, J=10 and 3Hz), 3.39 (m, 1H), 2.73 (dd, 1H, J=15 and 3Hz), 2.63 (m, 1H), 2.01–1.20 (m), 1.15 (s, 6H), 0.96 (d, 3H, J=4Hz), 0.85 (t, 3H, J=6Hz) 0.83 (d, 3H, J=7Hz).
Elemental Anal. C$_{25}$H$_{44}$O$_7$•1.0H$_2$O
Calc'd: C, 63.26; H, 9.77
Found: C, 63.13; H, 9.51

Step 3: Preparation of
6(R)-[2-[6(R)-(1(S)-2,2-dimethylbutyryloxy-3(R)-methyl-4-p-toluene-sulfonyl-butane)-2(S)-methyl-5(R)-hydroxycyclohexyl-1(S)]ethyl]-4(R)-hydroxy-3,4,5,6-tetrahydro-2H-pyran-2-one. (4)

To a stirred solution of the triol 3 (100 mg, 0.22 mmol), pyridine (71 ml, 1.0 mmol), and dry CH$_2$Cl$_2$ (1.1 mL) at 0° C., was added p-toluenesulfonyl chloride (50 mg, 0.26 mmol). After 5 minutes the cooling bath was removed and the reaction stirred overnight. The reaction mixture was diluted with ethyl acetate, washed with H$_2$O and brine, dried (MgSO$_4$), and concentrated. Flash chromatography (silica, 8% acetone/CH$_2$Cl$_2$) furnished the desired product as a colorless foam.

$^1$H NMR (CDCl$_3$): δ7.75 (d, 2H, J=8Hz), 7.31 (d, 2H, J=8Hz), 5.45 (m, 1H), 4.66 (m, 1H), 4.33 (m, 1H), 4.02 (dd, 1H, J=10 and 5Hz), 3.79 (dd, 1H, J=10 and 4Hz), 3.32 (m, 1H), 2.63 (m, 2H), 2.40 (S, 3H), 2.00–1.20 (m), 1.10 (S, 6H), 0.90 (d, 3H, J=7Hz), 0.80 (d, 3H, J=7Hz), 0.78 (t, 3H, J=7Hz)

Step 4: Preparation of
6(R)-[2-[6(R)-(1(S)-2,2-dimethylbutyryloxy-3(R)-methyl-4-iodobutane)-2(S)-methyl-5(R)-hydroxy-cyclohexyl]-1(S)]ethyl]-4(R)-hydroxy-3,4,5,6-tetrahydro2H-pyran-2-one. (5)

A stirred mixture of the tosylate 4 (0.80 g, 1.3 mmol), NaI (1.2 g, 7.8 mmol), and acetone (8.0 mL) was heated to reflux for 2.0 h. The cooled reaction mixture was diluted with ether, washed sequentially with H$_2$O, 10% Na$_2$SO$_3$, and brine, dried (MgSO$_4$), and concentrated. Flash chromatography (silica, ether) gave the desired product 5 as a colorless oil.

$^1$H NMR (CDCl$_3$): δ5.44 (m, 1H), 4.68 (m, 1H), 4.37 (m, 1H), 3.40 (m, 1H), 3.32 (dd, 1H, J=15 and 5 Hz), 3.25 (dd, 1H, J=15 and 3 Hz), 2.70 (dd, 1H, J=15 and 4 Hz), 2.61 (m, 1H), 2.00–1.28 (m), 1.13 (S, 6H), 0.98 (d, 3H, J=7Hz), 0.83 (t, 3H, J=7Hz), 0.82 (d, 3H, J=7Hz)

Step 5: Preparation of
6(R)-[2-[6(R)-(1(S)-2,2-dimethylbutyryloxy-3(R)-methyl-4-o-nitrophenylseleno-butane)-2(S)-methyl-5(R)hydroxy-cyclohexyl-1(S)]ethyl]-e(R)-hydroxy-3,4,5,6-tetrahydro-2H-pyran-2-one. (6)

A stirred solution of the iodide 5 (208 mg, 0.37 mmol), 2-nitrophenyl selenocyanate (167 mg, 0.75 mmol), and dry DMF (2.0 ml) was degassed, cooled to 0° C. and then treated with NaBH$_4$ (14 mg, 0.37 mmol). After 10 minutes the cooling bath was removed and the mixture stirred for 2.0 hours. The reaction mixture was diluted with ethyl acetate, washed with H$_2$O and brine, dried (MgSO$_4$), and concentrated. Flash chromatography (silica, 70% EtOAc/hexane) afforded the desired product 6 as a yellow oil.

$^1$H NMR (CDCl$_3$): δ8.23 (m, 1H), 7.54 (m, 2H), 7.28 (m, 1H), 5.60 (m, 1H), 4.67 (m, 1H), 4.38 (m, 1H), 3.35

(m, 1H), 3.05 (dd, 1H, J=11 and 4Hz), 2.80 (dd, 1H, J=11 and 4 Hz), 2.68 (m, 2H), 2.00–1.30 (m), 1.55 (S, 3H), 1.54 (d, 3H), 1.16 (d, 3H), 1.14 (S, 3H), 0.81 (t, J=6Hz)

Step 6: Preparation of 6(R)-[2-[6(R)-(1(S)-2,2-dimethylbutyryloxy-3-methyl-3-butene)-2(S)-methyl-5(R)-hydroxy-cyclohexyl-1(S)]ethyl]-4(R)-hydroxy-3,4,5,6-tetrahydro-2H-pyran-2-one. (7)

To a stirred solution of the selenide 6 (250 mg, 0.33 mmol) in THF (3 ml) at 0° C. was added 30% $H_2O_2$ (75 μl, 0.66 mmol) dropwise. After 5 minutes the cooling bath was removed and the reaction mixture stirred overnight. The orange solution was diluted with ethyl acetate, washed with sat. $NaHCO_3$ and brine, dried ($MgSO_4$), and concentrated. Flash chromatography (silica, ether) furnished the desired product 7 as an oil.
$^1H$ NMR ($CDCl_3$): δ5.48 (m, 1H), 4.78 (d, 2H, J=5Hz), 4.70 (m, 1H), 4.40 (m, 1H), 3.43 (m, 1H), 2.74 (dd, 1H, J=16 and 3Hz), 2.64 (m, 1H), 2.55–2.27 (m, 2H), 2.05–1.24 (m), 1.15 (s, 6H), 0.85 (d, 3H, J=7Hz), 0.84 (t, 3H, J=7Hz).
Elemental Anal. $C_{25}H_{42}O_6 \bullet 0.5\ H_2O$:
Calc'd: C, 67.08; H, 9.68
Found: C, 66.91; H, 9.61

Step 7: (a) Preparation of 6(R)-[2-[8(S)-(2,2-dimethylbutyryloxy)-2(S)-methyl-5-oxa-6(S)-(iodomethyl, methyl)-1,2,3,4,4a(R),7,8,8a-(R)-octahydronaphthyl-1(S)]ethyl]-4(R)-hydroxy-3,4,5,6-tetrahydro-2H-pyran-2-one(8a)

(b) 6(R)-[2-[8(S)-(2,2-dimethylbutyryloxy)-2(S)-methyl-5-oxa-6(R)-(iodomethyl, methyl)-1,2,3,4,4a(R),7,8,8a(R)-octahydronaphthyl-1(S)ethyl]-4(R)-hydroxy-3,4,5,6-tetrahydro-2H-pyran-2-one. (8b)

A stirred mixture of the olefin 7 (149 mg, 0.34 mmol), $NaHCO_3$ (115 mg, 1.3 mmol), and $CH_2Cl_2$ (3.4 mL) at 0° C. was treated with iodine (173 mg, 0.68 mmol) in one portion. After 15 minutes the dark red mixture was diluted with ethyl acetate, washed sequentially with $H_2O$, 10% $Na_2SO_3$, and brine, dried ($MgSO_4$), and concentrated. Flash chromatography (silica, ether) afforded the crude product 8 (1:1 mixture of epimers) as a red oil.
$^1H$ NMR of mixture ($CDCl_3$): δ5.20 (m, 1H), 4.58 (m, 1H), 4.35 (m, 1H), 3.79 (d, 0.5H, J=8Hz), 3.61 (m, 0.5H), 3.48 (m, 0.5H), 3.34 (d, 0.5H, J=8Hz), 3.17 (m, 1H), 2.71 (dd, 1H, J=15 and 5Hz), 2.30–1.10 (m), 0.84 (m, 6H).

Step 8: 6(R)-[2-[8(S)-(2,2-dimethylbutyryloxy)-2(S)-methyl-5-oxa-6,6-dimethyl-1,2,3,4,4a(R),7,8,-8a(R)-octahydronaphthyl-1(S)]ethyl]-4(R)-hydroxy-3,4,5,6-tetrahydro-2H-pyran-2-one. (9)

A stirred mixture of iodides 8 (153 mg, 0.27 mmol), tributyltin hydride (237 μl, 0.81 mmol), and azaisobutyronitrile (AIBN) (2 mg) in degassed toluene (1.4 ml) was heated at 80° C. for 4.0 hours. The cooled reaction mixture was concentrated to dryness. The residue was dissolved in $CH_3CN$ (10 ml) and washed with hexanes (10X).
The hexane washes, containing tin byproducts, were decanted away from the acetonitrile. The acetonitrile was evaporated and the residue subjected to flash chromatography (silica, 20% EtOAc/$CH_2Cl_2$) to furnish the crude product. The crude material was purified by preparative plate (0.5 mm, silica, 20% EtOAc/$CH_2Cl_2$) chromatography to yield the desired product 9 as a colorless oil.
$^1H$ NMR ($CDCl_3$): δ5.20 (m, 1H), 4.59 (m, 1H), 4.37 (m, 1H), 3.63 (m, 1H), 2.73 (dd, 1H, J=16 and 4Hz), 2.61 (m, 1H), 2.00–1.15 (m), 1.32 (S, 3H), 1.27 (S, 3H), 1.25 (S, 3H), 1.24 (S, 3H), 0.87 (d, 3H, J=6Hz), 0.84 (t, 3H, J=7Hz)
Elemental Anal. $C_{25}H_{42}O_6 \bullet 1.0H_2O$
Calc'd: C, 67.23; H, 9.93
Found: C, 66.87; H, 9.61

EXAMPLE 2

Preparation of 6(R)-[2-[8(S)-(2,2-dimethylbutyryloxy)-2(S)-methyl-5-oxa-6(S)-(phenylthiomethyl, methyl)-1,-2,3,4,4a(R),7,8,8a(R)-octahydronaphthyl-1(S)]ethyl]-4(R)-hydroxy-3,4,5,6-tetrahydro-2H-pyran-2-one. (10)
6(R)-[2-[8(S)-(2,2-dimethylbutyryloxy)-2(S)-methyl-5-oxa-6(R)-(phenylthiomethyl, methyl)-1,2,3,4,4a(R),7,-8,8a(R)-octahydronaphthyl-1(S)]ethyl]-4(R)-hydroxy-3,4,5,6-tetrahydro-2H-pyran-2-one. (11)

Steps 1–7 were repeated following the procedure of Example 1.

Step 8: Preparation of 6(R)-[2-[8(S)-(2,2-dimethylbutyryloxy)-2(S)-methyl-5-oxa-6(S)-(phenylthiomethyl, methyl)-1,2,3,4,4a(R),7,8,8a(R)-octahydronaphthyl-1(S)]ethyl]-4(R)-hydroxy-3,4,5,6-tetrahydro-2H-pyran-2-one. (10)

6(R)-[2-[8(S)-(2,2-dimethylbutyryloxy)-2(S)-methyl-5-oxa-6(R)-(phenylthiomethyl, methyl)-1,2,3,4,4a(R),7,-8,8a(R)-octahydronaphthyl-1(S)]ethyl]-4(R)-hydroxy-3,4,5,6-tetrahydro-2H-pyran-2-one. (11)

A degassed solution of iodides 8 (120 mg, 0.21 mmol), thiophenol (110 μl, 1.0 mmol), 1,8-diazabicyclo[5.4.-0]undec-7-ene (150 μl, 1.0 mmol), and dry DMF was heated at 80° C. for 4.0 hours. The cooled reaction mixture was diluted with ether, washed with $H_2O$ (2X) and brine, dried ($MgSO_4$), and concentrated. Flash chromatography (silica, 80% EtOAc/hexane) gave a 1:1 mixture of epimers as a colorless oil. Separation of the epimers was accomplished by preparative plate chromatography (0.5 mm silica, 65% EtOAc/benzene) to furnish the faster moving α-epimer 10 and the slower moving β-epimer 11 as colorless oils.

α-epimer: $^1H$ NMR ($CDCl_3$): δ7.40–7.10 (m, 5H), 5.23 (bs, 1H), 4.56 (m, 1H), 4.34 (m, 1H), 3.62 (m, 1H), 3.06 (d, 1H, J=13Hz), 2.95 (d, 1H, J=13Hz), 2.70 (dd, 1H, J=15 and 5Hz), 2.58 (dd, 1H, J=15 and 2Hz), 2.14 (m, 1H), 2.00–1.14 (m), 1.40 (S, 3H), 1.17 (S, 3H), 1.16 (S, 3H), 0.84 (d, 3H, J=7Hz), 0.83 (t, 3H, J=7Hz)

β-epimer: $^1H$ NMR ($CDCl_3$): δ7.40–7.10 (m, 5H), 5.20 (m, 1H), 4.56 (m, 1H), 4.33 (m, 1H), 3.64 (d, 1H, J=12Hz), 3.48 (m, 1H), 3.04 (d, 1H, J=12Hz), 2.70 (dd, 1H, J=15 and 5Hz), 2.58 (m, 1H), 2.22–1.10 (m), 1.29 (S, 3H), 1.13 (S, 3H), 1.12 (S, 3H), 0.83 (d, 3H, J=7Hz), 0.82 (t, 3H, J=7Hz).

EXAMPLE 3

Preparation of 6(R)-[8(S)-(2-methylbutyryloxy)-2(S)-methyl-5-oxa-6,6-dimethyl-1,2,3,4,4a(R),7,8,8a(R)-octahydronaphthyl-1(S)ethyl]-4(R)-hydroxy-3,4,5,6-tetrahydro-2H-pyran-2-one. (12)

Utilizing the general procedure of Example 1 but substituting 6(R)-[2-8(S)-(2-methylbutyryloxy)-2(S)-methyl-6(R)-methyl-1,2,6,7,8,8a(R)-hexahydronaphthyl-1(S)]ethyl]-4(R)-hydroxy-3,4,5,6-tetrahydro-2H-pyran-2-one, for the starting polyhydronaphthyl moiety, the titled compound is prepared.

What is claimed is:

1. A compound of structural formula B:

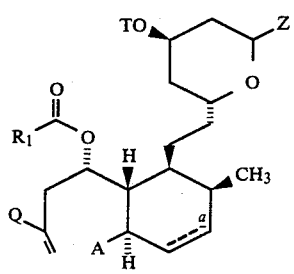

wherein:
A is HO, SH or HN—$R_N$;
Q is $CH_3$, $CH_2OT$, or H;
T is H, tert-butyldimethylsilyl, tert-butyldiphenylsilyl, trimethylsilyl, triethylsilyl, triisopropylsilyl or tetrahydropyranyl;
Z is $OCH_3$, or Z together with the carbon to which it is attached represents C=O;
$R_1$ is selected from:
 (1) $C_{1-10}$ alkyl;
 (2) substituted $C_{1-10}$ alkyl in which one or more substituent(s) is selected from
  (a) halogen,
  (b) hydroxy,
  (c) $C_{1-10}$ alkoxy,
  (d) $C_{1-5}$ alkoxycarbonyl,
  (e) $C_{1-5}$ acyloxy,
  (f) $C_{3-8}$ cycloalkyl,
  (g) phenyl,
  (h) substituted phenyl in which the substituents are X and Y,
  (i) $C_{1-10}$ alkylS(O)$_n$ in which n is 0 to 2,
  (j) $C_{3-8}$ cycloalkylS(O)$_n$,
  (k) phenylS(O)$_n$,
  (l) substituted phenylS(O)$_n$ in which the substituents are X and Y, and
  (m) oxo;
 (3) $C_{1-10}$ alkoxy;
 (4) $C_{2-10}$ alkenyl;
 (5) $C_{3-8}$ cycloalkyl;
 (6) substituted $C_{3-8}$ cycloalkyl in which one substituent is selected from
  (a) $C_{1-10}$ alkyl,
  (b) substituted $C_{1-10}$ alkyl in which the substituent is selected from
   (i) halogen,
   (ii) hydroxy,
   (iii) $C_{1-10}$ alkoxy,
   (iv) $C_{1-5}$ alkoxycarbonyl,
   (v) $C_{1-5}$ acyloxy,
  (vi) phenyl,
   (vii) substituted phenyl in which the substituents are X and Y
   (viii) $C_{1-10}$ alkylS(O)$_n$,
   (ix) $C_{3-8}$ cycloalkylS(O)$_n$,
   (x) phenylS(O)$_n$,
   (xi) substituted phenylS(O)$_n$ in which the substituents are X and Y, and
   (xii) oxo,
  (c) $C_{1-10}$ alkylS(O)$_n$,
  (d) $C_{3-8}$ cycloalkylS(O)$_n$,
  (e) phenylS(O)$_n$,
  (f) substituted phenylS(O)$_n$ in which the substituents are X and Y,
  (g) halogen,
  (h) hydroxy,
  (i) $C_{1-10}$ alkoxy,
  (j) $C_{1-5}$ alkoxycarbonyl,
  (k) $C_{1-5}$ acyloxy,
  (l) phenyl, and
  (m) substituted phenyl in which the substituents are X and Y;
 (7) phenyl;
 (8) substituted phenyl in which the substituents are X and Y;
 (9) amino;
 (10) $C_{1-5}$ alkylamino;
 (11) di($C_{1-5}$ alkyl)amino;
 (12) phenylamino;
 (13) substituted phenylamino in which the substituents are X and Y;
 (14) phenyl $C_{1-10}$ alkylamino;
 (15) substituted phenyl $C_{1-10}$ alkylamino in which the substituents are X and Y;
 (16) $R_5S$ in which $R_5$ is selected from
  (a) $C_{1-10}$ alkyl,
  (b) phenyl, and
  (c) substituted phenyl in which the substituents are X and Y;
$R_N$ is selected from:
 (a) $C_{1-5}$ alkyl;
 (b) phenyl$C_{1-5}$alkyl;
X and Y independently are hydrogen, halogen, trifluoromethyl, $C_{1-3}$ alkyl, nitro, cyano or group selected from:
 (1) $R_6O(CH_2)_m$ in which m is 0 to 3 and $R_6$ is hydrogen, $C_{1-3}$alkyl or hydroxy-$C_{2-3}$alkyl; (2)

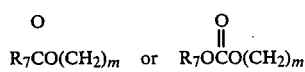

in which $R_7$ is hydrogen, $C_{1-3}$alkyl, hydroxy-$C_{2-3}$alkyl, phenyl, naphthyl, amino-$C_{1-3}$alkyl, $C_{1-3}$alkylamino-$C_{1-3}$alkyl, di($C_{1-3}$alkyl)amino-$C_{1-3}$alkyl, hydroxy-$C_{2-3}$ alkylamino-$C_{1-3}$alkyl or di(hydroxy-$C_{2-3}$alkyl) amino-$C_{1-3}$alkyl; provided that in

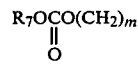

$R_7$ is not H;
(3)

in which $R_8$ is hydrogen, $C_{1-3}$alkyl, hydroxy-$C_{2-3}$ alkyl, $C_{1-3}$alkoxy-$C_{1-3}$alkyl, phenyl or naphthyl;

(4)

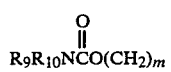

in which $R_9$ and $R_{10}$ independently are hydrogen, $C_{1-3}$ alkyl, hydroxy-$C_{2-3}$alkyl (5) $R_{11}S(O)_n(CH_2)_m$ in which $R_{11}$ is hydrogen, $C_{1-3}$alkyl, amino, $C_{1-3}$alkylamino or di($C_{1-3}$alkyl)amino;

a is a single bond or a double bond;
halogen is F or Cl;
n is 0 to 2.

2. A compound of claim 1 wherein:
A is HO or SH.

3. A compound of claim 2 wherein:
$R_1$ is selected from:
  (1) $C_{1-10}$ alkyl;
  (2) substituted $C_{1-10}$ alkyl in which one or more substituent(s) is selected from
    (a) halogen,
    (b) hydroxy,
    (c) $C_{1-10}$ alkoxy,
    (d) $C_{1-5}$ alkoxycarbonyl,
    (e) $C_{1-5}$ acyloxy,
    (f) $C_{3-8}$ cycloalkyl,
    (g) phenyl,
    (h) substituted phenyl in which the substituents are X and Y, and
    (i) oxo;
  (3) $C_{3-8}$ cycloalkyl;
  (4) substituted $C_{3-8}$ cycloalkyl in which one substituent is selected from
    (a) $C_{1-10}$ alkyl,
    (b) substituted $C_{1-10}$ alkyl in which the substituent is selected from
      (i) halogen,
      (ii) hydroxy,
      (iii) $C_{1-10}$ alkoxy,
      (iv) $C_{1-5}$ acyloxy,
      (v) $C_{1-5}$ alkoxycarbonyl,
      (vi) phenyl,
      (vii) substituted phenyl in which the substituents are X and Y, and
      (viii) oxo,
    (c) halogen,
    (d) hydroxy,
    (e) $C_{1-10}$ alkoxy,
    (f) $C_{1-5}$ alkoxycarbonyl,
    (g) $C_{1-5}$ acyloxy,
    (h) phenyl,
    (i) substituted phenyl in which the substituents are X and Y;
  (5) phenylamino;
  (6) substituted phenylamino in which the substituents are X and Y;
  (7) phenyl $C_{1-10}$ alkylamino; and
  (8) substituted phenyl $C_{1-10}$ alkylamino in which the substituents are X and Y.

4. A compound of claim 3 wherein:
$R_1$ is selected from:
  (1) $C_{1-10}$ alkyl;
  (2) $C_{3-8}$ cycloalkyl;
  (3) phenylamino; and
  (4) substituted phenylamino in which the substituents are X and Y.

5. A compound of claim 4 wherein:
$R_1$ is $C_{1-10}$alkyl;
Q is $CH_3$; and
a is a single bond.

6. A compound of claim 5 wherein:
T is tert-butyldimethylsilyl;
$R_1$ is 2-methyl-2-butyl or 2-butyl.

7. A compound of claim 6 selected from the group wherein:
  (1) $R_1$ is 2-methyl-2-butyl, A is OH, Z together with the carbon to which it is attached is C=O;
  (2) $R_1$ is 2-butyl, A is OH, Z together with the carbon to which it is attached is C=O;
  (3) $R_1$ is 2-methyl-2-butyl, A is SH, Z is $OCH_3$;
  (4) $R_1$ is 2-butyl, A is SH, Z is $OCH_3$.

8. A compound of claim 1 wherein:
A is $HNR_N$;
Z together with the carbon to which it is attached is C=O.

9. A compound of claim 8 wherein:
$R_1$ is selected from:
  (1) $C_{1-10}$ alkyl;
  (2) substituted $C_{1-10}$ alkyl in which one or more substituent(s) is selected from
    (a) halogen,
    (b) hydroxy,
    (c) $C_{1-10}$ alkoxy,
    (d) $C_{1-5}$ alkoxycarbonyl,
    (e) $C_{1-5}$ acyloxy,
    (f) $C_{3-8}$ cycloalkyl,
    (g) phenyl,
    (h) substituted phenyl in which the substituents are X and Y, and
    (i) oxo;
  (3) $C_{3-8}$ cycloalkyl;
  (4) substituted $C_{3-8}$ cycloalkyl in which one substituent is selected from
    (a) $C_{1-10}$ alkyl,
    (b) substituted $C_{1-10}$ alkyl in which the substituent is selected from
      (i) halogen,
      (ii) hydroxy,
      (iii) $C_{1-10}$ alkoxy,
      (iv) $C_{1-5}$ acyloxy,
      (v) $C_{1-5}$ alkoxycarbonyl,
      (vi) phenyl,
      (vii) substituted phenyl in which the substituents are X and Y, and
      (viii) oxo,
    (c) halogen,
    (d) hydroxy,
    (e) $C_{1-10}$ alkoxy,
    (f) $C_{1-5}$ alkoxycarbonyl,
    (g) $C_{1-5}$ acyloxy,
    (h) phenyl,
    (i) substituted phenyl in which the substituents are X and Y;
  (5) phenylamino;

(6) substituted phenylamino in which the substituents are X and Y;
(7) phenyl C$_{1-10}$ alkylamino; and
(8) substituted phenyl C$_{1-10}$ alkylamino in which the substituents are X and Y.

10. A compound of claim 9 wherein:
R$_1$ is selected from:
(1) C$_{1-10}$ alkyl;
(2) C$_{3-8}$ cycloalkyl;
(3) phenylamino; and
(4) substituted phenylamino in which the substituents are X and Y.

11. A compound of claim 10 wherein:
R$_1$ is C$_{1-10}$alkyl;
Q is CH$_3$; and
a is a single bond.

12. A compound of claim 11 wherein:
T is tert-butyldimethylsilyl;
R$_1$ is 2-methyl-2-butyl or 2-butyl;
R$_N$ is phenylCH$_2$—.

13. A compound of claim 12 selected from the group wherein:
(a) R$_1$ is 2-methyl-2-butyl;
(b) R$_1$ is 2-butyl.

14. A process for the formation of a compound (B) of claim 1:

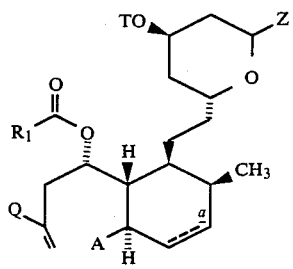

which comprises:
(i) Treating the compound (1—1)

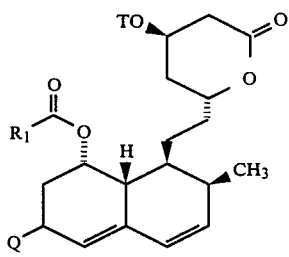

wherein R$_1$, and Q are defined above, with a tris(triarylphosphine) rhodium halide in the presence of H$_2$ to form a compound of formula (1-2);

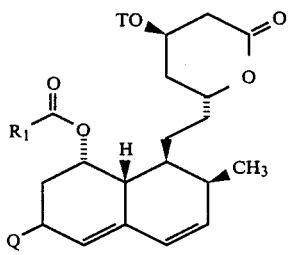

(ii) Treating compound (1-2) with ozone in an alcoholic solvent followed by reduction of the ozonide with zinc/acetic acid and reduction of the intermediate ketoaldehyde with sodium borohydride to yield compound (1-3);

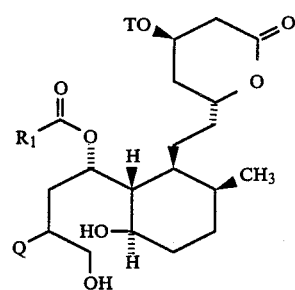

(iii) Contacting compound (1-3) with an iodinating reagent to form compound (1-4);

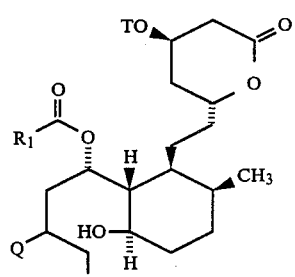

(iv) Treating compound (1-4) with a 2-nitrophenyl selenocyanate and NaBH$_4$ to yield a compound (1-5);

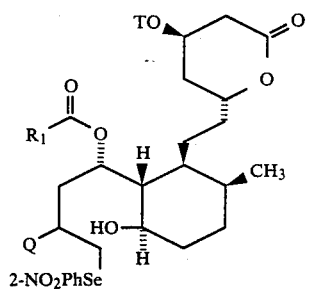

(v) Treating compound (1-5) with H$_2$O$_2$/THF to yield compound (1-6);

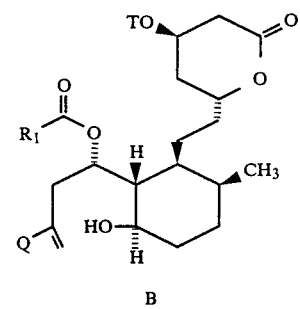

provided that where a is a double bond the ketoaldehyde formed in step (ii) is isolated and reduced with one equivalent sodium borohydride to yield a ketoalcohol (3—3);

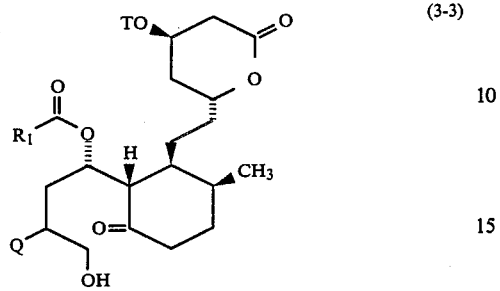
(3-3)

followed by treatment of compound (3—3) with PdCl$_2$/Pd(OAc)$_2$ to yield the unsaturated ketoalcohol (3-4); then

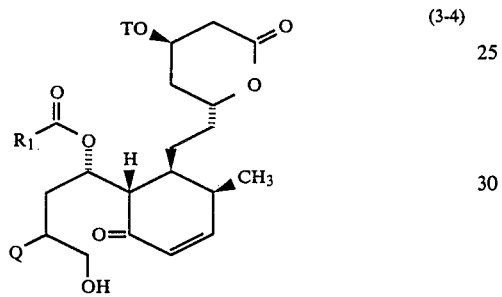
(3-4)

(iia) treatment of compound (3-4) with sodium borohydride to yield compound (3-5); followed by

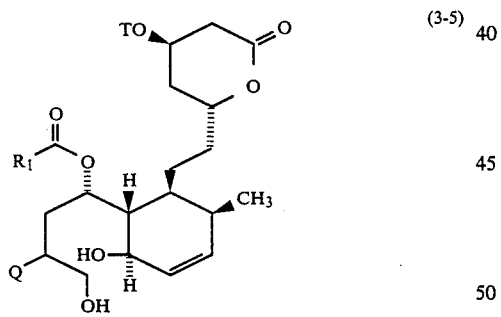
(3-5)

treatment of compound (3-5) in steps (iii) to step (v) to yield a compound of formula (B);

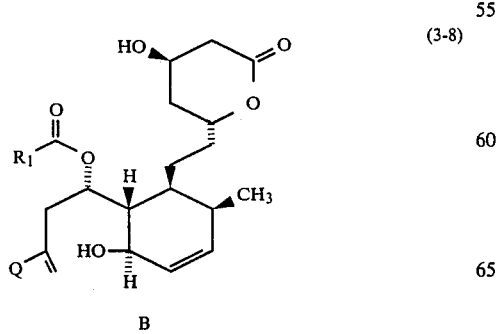
(3-8)

B and provided that where A is SH the process further comprises:

(vi) Contacting compound (1-6) with diisobutylaluminum hydride (dibal) to yield compound (4-7);

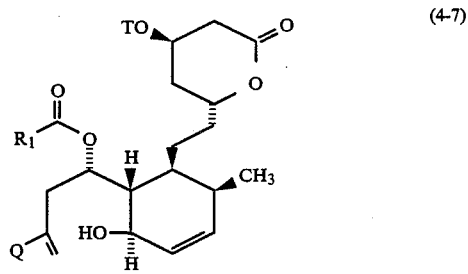
(4-7)

(vii) treating compound (4-7) with methanol and para-toluene sulfonic acid (PTSA) to yield compound (4-8);

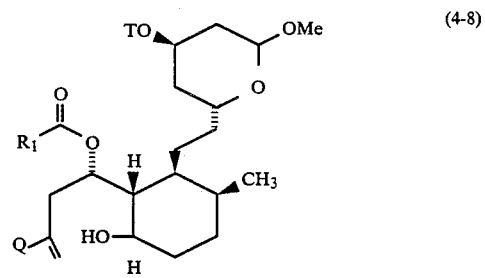
(4-8)

(viii) treating compound (4-8) with (COCl)$_2$ and dimethylsulfoxide (DMSO) and a base to yield compound (4-9);

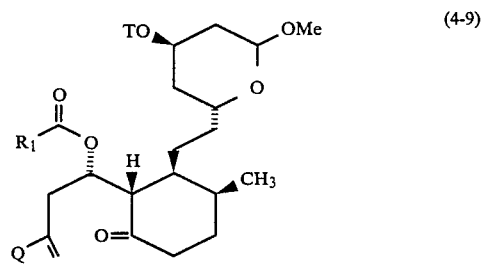
(4-9)

(ix) treating compound (4-9) with PdCl$_2$/Pd(OAc)$_2$ to yield the enone compound (4-10);

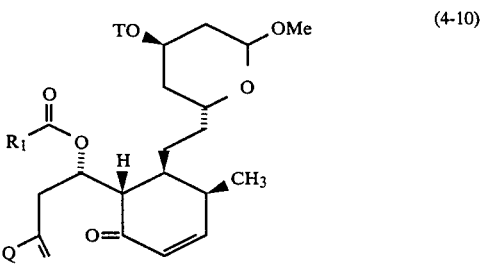
(4-10)

(x) treating compound (4-10) with 2,4-bis(4-methoxyphenyl)-1,3,2,4-dithiadiphosphetane-2,4-disulfide to yield the thiaketone (4-11);

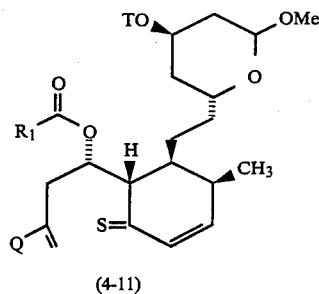

(4-11)

(xi) treating compound (4-11) with a thiaketone reducing agent to yield the intermediate (B) (4-12);

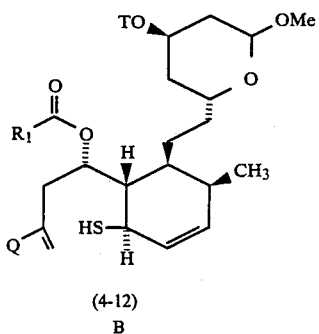

(4-12)
B provided that where a is a single bond step (ix) is ommitted; and provided that where A is HNR$_N$ the process further comprises:
(xii) treating compound (1-6) with (ClCO)$_2$ in DMSO and a base to yield compound (5-7);

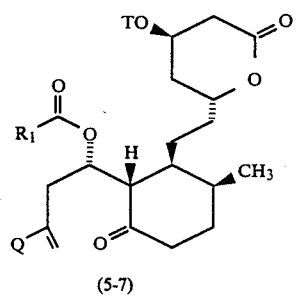

(5-7)

(xiii) contacting compound (5-7) with R$_N$NH$_2$ and NaCNBH$_3$ to yield an intermediate (B) (5-8);

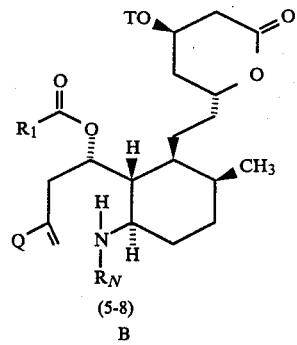

(5-8)
B provided that where A is HNR$_N$ and a is a double bond the process further comprises treating compound (5-7) from step (xii) with PdCl$_2$/Pd(OAc)$_2$ (Step Xiiia) to yield compound (5-7a);

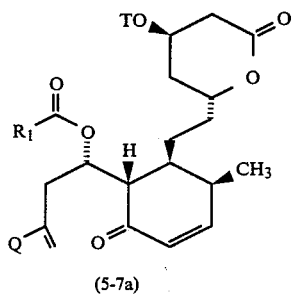

(5-7a)

followed by step (xiii) to yield compound (5-8a) of formula (B).

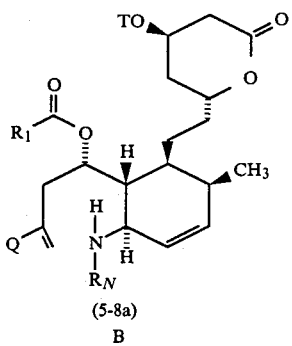

(5-8a)
B

* * * * *